United States Patent
Thai et al.

(10) Patent No.: US 12,290,536 B2
(45) Date of Patent: May 6, 2025

(54) COMPOSITION AND METHODS FOR PRODUCING INSULIN PRODUCING ISLET CELLS

(71) Applicant: IMAGINE PHARMA LLC, Devon, PA (US)

(72) Inventors: Ngoc Thai, Pittsburgh, PA (US); Jonathan Pollett, Pittsburgh, PA (US)

(73) Assignee: Imagine Pharma LLC, Pittsburgh, PA (US)

( * ) Notice: Subject to any disclaimer, the term of this patent is extended or adjusted under 35 U.S.C. 154(b) by 1040 days.

(21) Appl. No.: 17/256,141

(22) PCT Filed: Jun. 20, 2019

(86) PCT No.: PCT/US2019/038305
§ 371 (c)(1),
(2) Date: Dec. 24, 2020

(87) PCT Pub. No.: WO2020/005721
PCT Pub. Date: Jan. 2, 2020

(65) Prior Publication Data
US 2021/0205371 A1 Jul. 8, 2021

Related U.S. Application Data

(60) Provisional application No. 62/689,780, filed on Jun. 25, 2018.

(51) Int. Cl.
*A61K 35/39* (2015.01)
*C12N 5/00* (2006.01)
*C12N 5/071* (2010.01)

(52) U.S. Cl.
CPC ............ *A61K 35/39* (2013.01); *C12N 5/0678* (2013.01); *C12N 2501/998* (2013.01)

(58) Field of Classification Search
CPC . A61K 35/39; C12N 5/0678; C12N 2501/998
See application file for complete search history.

(56) References Cited

U.S. PATENT DOCUMENTS

| 2004/0157328 A1 | 8/2004 | Roubin |
| 2011/0014160 A1 | 1/2011 | Hald |

OTHER PUBLICATIONS

Lee et al. (2013) "Expansion and conversion of human pancreatic ductal cells into insulin-secreting endocrine cells" eLife, 2, e00940, 22 pages. (Year: 2013).*
Bottino et al. (Jul. 1, 2018) "IMG-1 Activates and Mobilizes Insulin-Producing Islet Progenitor Cells (CD133+/Insulin+) In Vitro" Diabetes, 67(Supplement_1):309-LB. (Year: 2018).*
Lee et al., Expansion and conversion of human pancreatic ductal cells into insulin-secreting endocrine cells, eLife 2013;2:e00940. DOI: 10.7554/eLife.00940.

* cited by examiner

*Primary Examiner* — Laura Schuberg
*Assistant Examiner* — James Joseph Graber

(57) ABSTRACT

Disclosed herein are compositions and methods to differentiate pancreatic cells into functional insulin-producing CD133/Ki-67-positive activated islet proliferating cells (AIPCs) derived from isolated pancreatic islets and expand derived-AIPCs in in vitro cultures using a culture medium comprising an active agent. Also disclosed herein is the use of the AIPCs for implantation into a mammal for in vivo therapy, specifically for pancreatic disorders, including diabetes type I.

6 Claims, 16 Drawing Sheets
Specification includes a Sequence Listing.

+IMG

SEQUENCE LISTING

```
<160> NUMBER OF SEQ ID NOS: 4

<210> SEQ ID NO 1
<211> LENGTH: 293
<212> TYPE: PRT
<213> ORGANISM: HOMO SAPIEN

<400> SEQUENCE: 1

Met Ala Asp Ala Gly Ala Ala Gly Pro Gly Gly Pro Gly Gly
1               5                   10                  15

Pro Gly Met Gly Asn Arg Gly Gly Phe Arg Gly Gly Phe Gly Ser Gly
                20                  25                  30

Ile Arg Gly Arg Gly Arg Gly Arg Gly Arg Gly Arg Gly Arg
            35                  40                  45

Gly Ala Arg Gly Gly Lys Ala Glu Asp Lys Glu Trp Met Pro Val Thr
        50                  55                  60

Lys Leu Gly Arg Leu Val Lys Asp Met Lys Ile Lys Ser Leu Glu Glu
65                  70                  75                  80

Ile Tyr Leu Phe Ser Leu Pro Ile Lys Glu Ser Glu Ile Ile Asp Phe
                85                  90                  95

Phe Leu Gly Ala Ser Leu Lys Asp Glu Val Leu Lys Ile Met Pro Val
                100                 105                 110

Gln Lys Gln Thr Arg Ala Gly Gln Arg Thr Arg Phe Lys Ala Phe Val
            115                 120                 125

Ala Ile Gly Asp Tyr Asn Gly His Val Gly Leu Gly Val Lys Cys Ser
        130                 135                 140

Lys Glu Val Ala Thr Ala Ile Arg Gly Ala Ile Ile Leu Ala Lys Leu
145                 150                 155                 160

Ser Ile Val Pro Val Arg Arg Gly Tyr Trp Gly Asn Lys Ile Gly Lys
                165                 170                 175

Pro His Thr Val Pro Cys Lys Val Thr Gly Arg Cys Gly Ser Val Leu
                180                 185                 190

Val Arg Leu Ile Pro Ala Pro Arg Gly Thr Gly Ile Val Ser Ala Pro
            195                 200                 205

Val Pro Lys Lys Leu Leu Met Met Ala Gly Ile Asp Asp Cys Tyr Thr
            210                 215                 220

Ser Ala Arg Gly Cys Thr Ala Thr Leu Gly Asn Phe Ala Lys Ala Thr
225                 230                 235                 240

Phe Asp Ala Ile Ser Lys Thr Tyr Ser Tyr Leu Thr Pro Asp Leu Trp
                245                 250                 255

Lys Glu Thr Val Phe Thr Lys Ser Pro Tyr Gln Glu Phe Thr Asp His
                260                 265                 270

Leu Val Lys Thr His Thr Arg Val Ser Val Gln Arg Thr Gln Ala Pro
            275                 280                 285
```

Ala Val Ala Thr Thr
    290

<210> SEQ ID NO 2
<211> LENGTH: 159
<212> TYPE: PRT
<213> ORGANISM: HOMO SAPIENS

<400> SEQUENCE: 2

Gly His Val Gly Leu Gly Val Lys Cys Ser Lys Glu Val Ala Thr Ala
1               5                   10                  15

Ile Arg Gly Ala Ile Ile Leu Ala Lys Leu Ser Ile Val Pro Val Arg
            20                  25                  30

Arg Gly Tyr Trp Gly Asn Lys Ile Gly Lys Pro His Thr Val Pro Cys
        35                  40                  45

Lys Val Thr Gly Arg Cys Gly Ser Val Leu Val Arg Leu Ile Pro Ala
    50                  55                  60

Pro Arg Gly Thr Gly Ile Val Ser Ala Pro Val Pro Lys Lys Leu Leu
65                  70                  75                  80

Met Met Ala Gly Ile Asp Asp Cys Tyr Thr Ser Ala Arg Gly Cys Thr
                85                  90                  95

Ala Thr Leu Gly Asn Phe Ala Lys Ala Thr Phe Asp Ala Ile Ser Lys
            100                 105                 110

Thr Tyr Ser Tyr Leu Thr Pro Asp Leu Trp Lys Glu Thr Val Phe Thr
        115                 120                 125

Lys Ser Pro Tyr Gln Glu Phe Thr Asp His Leu Val Lys Thr His Thr
    130                 135                 140

Arg Val Ser Val Gln Arg Thr Gln Ala Pro Ala Val Ala Thr Thr
145                 150                 155

<210> SEQ ID NO 3
<211> LENGTH: 75
<212> TYPE: PRT
<213> ORGANISM: HOMO SAPIENS

<400> SEQUENCE: 3

Ser Ile Val Pro Val Arg Arg Gly Tyr Trp Gly Asn Lys Ile Gly Lys
1               5                   10                  15

Pro His Thr Val Pro Cys Lys Val Thr Gly Arg Cys Gly Ser Val Leu
            20                  25                  30

Val Arg Leu Ile Pro Ala Pro Arg Gly Thr Gly Ile Val Ser Ala Pro
        35                  40                  45

Val Pro Lys Lys Leu Leu Met Met Ala Gly Ile Asp Asp Cys Tyr Thr
    50                  55                  60

Ser Ala Arg Gly Cys Thr Ala Thr Leu Gly Asn
65                  70                  75

<210> SEQ ID NO 4
<211> LENGTH: 87
<212> TYPE: PRT
<213> ORGANISM: HOMO SAPIENS

<400> SEQUENCE: 4

Gly His Val Gly Leu Gly Val Lys Cys Ser Lys Glu Val Ala Thr Ala
1               5                   10                  15

Ile Arg Gly Ala Ile Ile Leu Ala Lys Leu Ser Ile Val Pro Val Arg
            20                  25                  30

Arg Gly Tyr Trp Gly Asn Lys Ile Gly Lys Pro His Thr Val Pro Cys

-continued

```
            35                  40                  45
Lys Val Thr Gly Arg Cys Gly Ser Val Leu Val Arg Leu Ile Pro Ala
    50                  55                  60

Pro Arg Gly Thr Gly Ile Val Ser Ala Pro Val Pro Lys Lys Leu Leu
65                  70                  75                  80

Met Met Ala Gly Ile Asp Asp
                85
```

COMPOSITION AND METHODS FOR PRODUCING INSULIN PRODUCING ISLET CELLS

CROSS REFERENCE TO RELATED APPLICATIONS

This application claims the benefit of U.S. Provisional Patent Application No. 62/689,780 filed on Jun. 25, 2018, which application is incorporated herein by reference in its entirety.

BACKGROUND

Diabetes is a metabolic disease defined by hyperglycemia but also leads to serious damage to many of the body's systems, including nerves, blood vessels, eyes, kidneys, heart, and more. Some studies estimate that there may be more than 400 million people worldwide living with diabetes, and the incidence and prevalence of diabetes is increasing throughout the globe, especially in the US, China, and India.

There are multiple variants of diabetes, but two main types predominate. In type 1 diabetes, the pancreas produces little or no insulin because of the loss of insulin-producing islet beta cells. These insulin-producing islet cells are present in type 2 diabetes, but the insulin produced is less in quantity and effectiveness because of insulin resistance. Thus, regardless of the variant, diabetes can be characterized as a dysfunction of islet cells.

The study of diabetes and islet biology has been severely limited by the inability to culture and expand islet cells. Currently, islet clusters or cells can only be maintained in culture for approximately 3 weeks, essentially in a deteriorating state precluding the long-term study of islet cells. This inability to culture and propagate islet cells also limits the capability of islet cell replacement therapy which is a potential cure for diabetes.

At present, the two current standard techniques to generate beta cells to provide a cell source for drug discovery and cell transplantation therapy in diabetes are: (i) the differentiation of non-beta islet cells such as induced-pluripotent stem (iPC) cells, or fibroblasts through genetic reprogramming and/or exposure to differentiation and multiple maturation factors, or by differentiating embryonic stem cells into beta-like cells; and (ii) the induction of proliferation of mature beta cells by the use of therapeutic molecules. The main drawbacks of the current approaches are associated with genetic manipulation, efficiency of differentiation, and potentially off-target effects of the chemicals used to trigger beta-cell proliferation. In addition, most approaches require long-culture and significant manipulation steps/times, which increase the risks of microbiological contaminations, significantly impact production cost, ultimately affecting clinical translation.

Previously, groups have attempted to generate insulin-producing pancreatic beta cells from stem cells in vitro as it is believed this would provide an unprecedented cell source for drug discovery and cell transplantation therapy in diabetes. In 2009 it was published in Cell Research a strategy to direct both human Embryonic Stem (ES) cells and human induced-pluripotent stem (iPS) cells to differentiate into mature insulin-producing cells similar to adult islet beta cells. To generate these iPS cells, somatic cells have to undergo episomal reprogramming by being subjected to multiple factors that include (and are not limited to), OCT4, SOX2, KLF4 and a short hairpin RNA against p53, and is a multi-step affair that takes several weeks to establish. The differentiated human ES cells at the final stage secreted C-peptide in response to glucose stimulation in a manner approaching that of adult human islets. Furthermore, the co-expression of C-peptide, PDX1 and NKX6-1 within induced insulin-producing cells was observed in vitro for the first time. To generate these cells, multiple reagents/factors are used and the protocol takes 2-3 weeks of a multiple step differentiation protocol to generate the cells.

In 2014, Pagliuca et. al, (Cell, Vol. 159: Issue 2, p. 428-439, Oct. 9, 2014) generated beta cells from human pluripotent stem cells (hPSC) in vitro using a scalable suspension-based culture system that can generate greater than 108 hPSCs and later differentiated cell types. Their protocol takes 4-5 weeks and involves a unique combination of sequential culture steps using factors that affect signaling in numerous pathways, including signaling by wnt, activin, hedgehog, EGF, TGFβ, thyroid hormone, and retinoic acid, as well as γ-secretase inhibition.

While in 2015, a group in California converted human fibroblasts towards an endodermal cell fate by employing episomal reprogramming factors in combination with specific growth factors and chemical compounds (Nat. Commun. 2016; 7:100080). These cells were further differentiated using chemical compounds that promote the differentiation and maturation into functional pancreatic beta-like cells in vitro. However, these cells have yet to provide a source of beta-cell replacement primarily because their severe manipulation requires the cells to be encapsulated in a device when implanted in vivo, their inability to generate all the cells in the islet that are necessary to appropriately regulate blood glucose, and the formation of teratomas within 7 weeks post transplantation.

The induction of proliferation of mature beta cells has previously been accomplished by the use of small-molecule inhibitors of dual-specificity tyrosine-regulated kinase 1A (DYRK1A) (Wang, et. Al, Cell Metab. 2019; 29:638-65). The use of DYRK1A inhibitors results in a proliferation index of 1.5%-3% in beta cells. More recently to promote the proliferation of mature beta cells, Wang et al. combined pharmacologic inhibition of DYRK1A and transforming growth factor beta superfamily (TGFbSF)/SMAD signaling generates remarkable further synergistic increases in human beta cell proliferation (average labeling index, 5%-8%, and as high as 15%-18%), and increases in both mouse and human beta cell numbers. To induce proliferation of mature beta cells, whole islets are used and do not generate cells outside of the islet. Cells are not mobilized and remain in the islet structure. To release the cells from the islets the islets were dissociated using 0.05% trypsin neutralized by the addition of an equal volume of 100% FBS. Though this work appears promising, the levels of proliferation observed is not sufficient to generate the number of insulin-producing cells necessary to generate a viable source of insulin-producing cells for therapeutic use, such as for the treatment of diabetes.

Both of the current standard techniques used to generate bona fide beta cells as a source for cell therapy or transplantation in diabetes are intensive, require multiple steps, myriad factors, and requires many weeks to generate the desired cells. Cell-based therapies offer the promise of treating and altering the course of diseases, such as diabetes type I, which cannot be addressed adequately by existing pharmaceuticals.

SUMMARY OF THE INVENTION

The compositions and methods described herein overcome problems of the aforementioned methods. Disclosed herein is an activated islet proliferating cell (AIPC) population and a method for preparing the same. The AIPC population is capable of producing insulin and enabling expansion of a population of pancreatic islets to meet demands for use in a cell-based therapy.

The methods described herein provide a rapid means to differentiate isolated pancreatic islets into an AIPC population having a certain percentage of islets (further described herein) that produce insulin and that have both a CD133 cell marker and a Ki-67-marker, which are identified herein as "triple positive" islets. The so-called "triple positive" islets are glucose responsive and secrete both insulin and glucagon in response to appropriate stimuli.

Representative cultures of said AIPCs have been deposited with ATTCC [Accession Number PTA-125942] under the terms of the Budapest Treaty.

Also disclosed herein is a method of treatment comprising administering an effective amount of an AIPC population to a mammal, e.g., human, to restore healthy pancreatic islets capable of producing insulin in response to glucose stimulation.

Figure 1A:
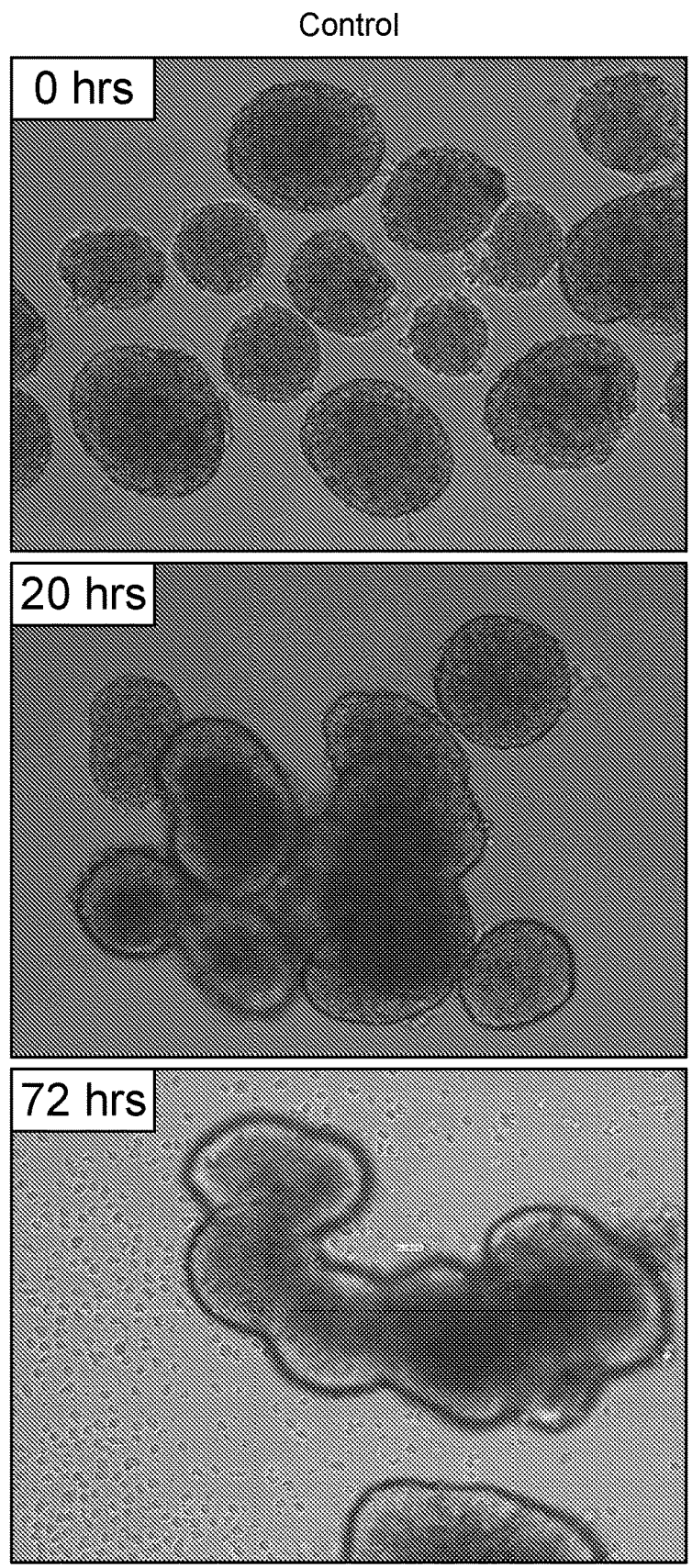
FIG. 1 shows microscopy images of cultured murine islets treated with a cell culture medium comprising IMG (≈3 μg/mL), as described further herein (see Table 2) compared to cultured murine islets cultured in base medium alone (see Table 3). Within 24 hours following treatment, the treated islets become less clustered and islet cells appeared to actively migrate away from the clusters. Control islets maintained their clustered morphology and displayed minimal evidence of cell migration. By 72 hours in culture, the treated islets had lost most of their morphology and have begun to establish colonies of insulin-producing CD133 positive, Ki-67 positive proliferating islet cells. (See Example 1)
Figure 1B:
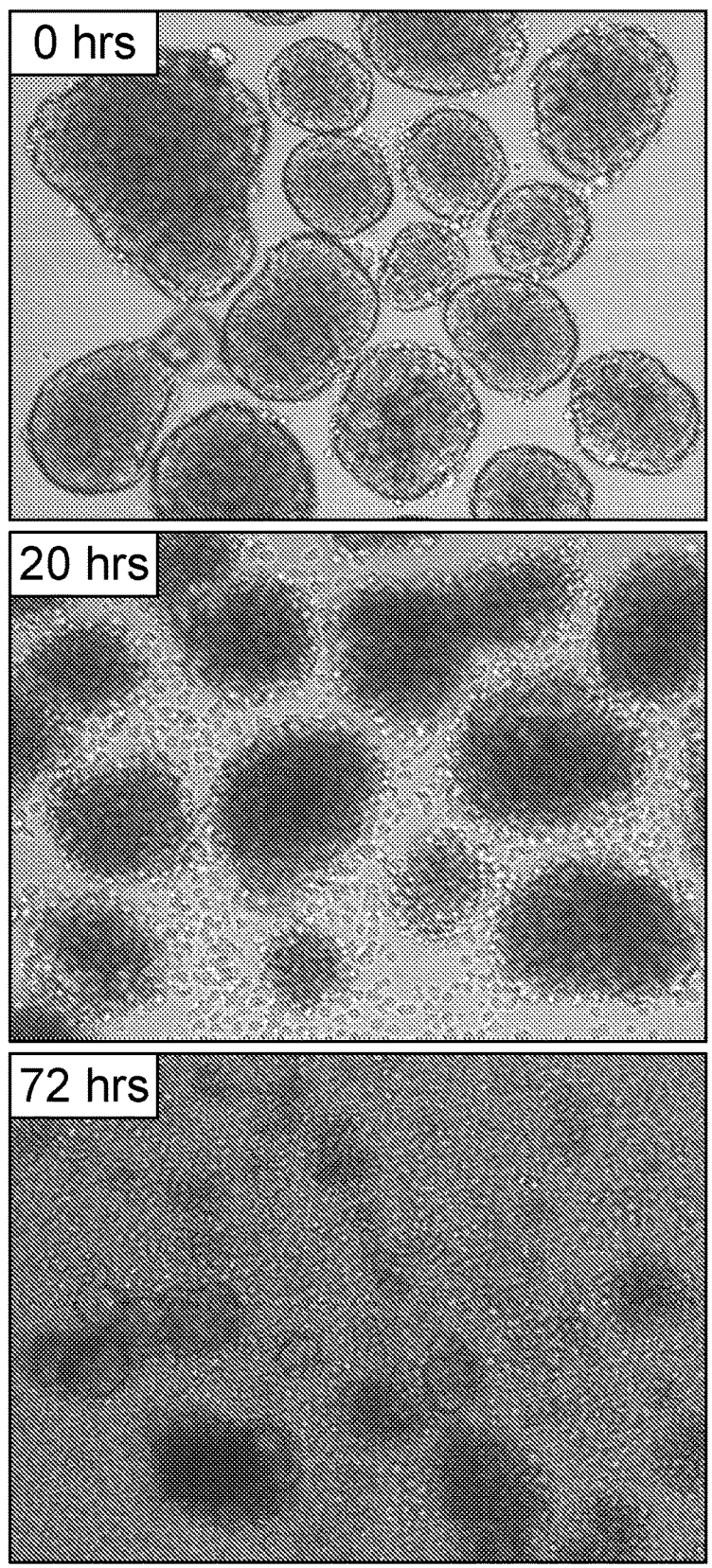
Figure 2A:
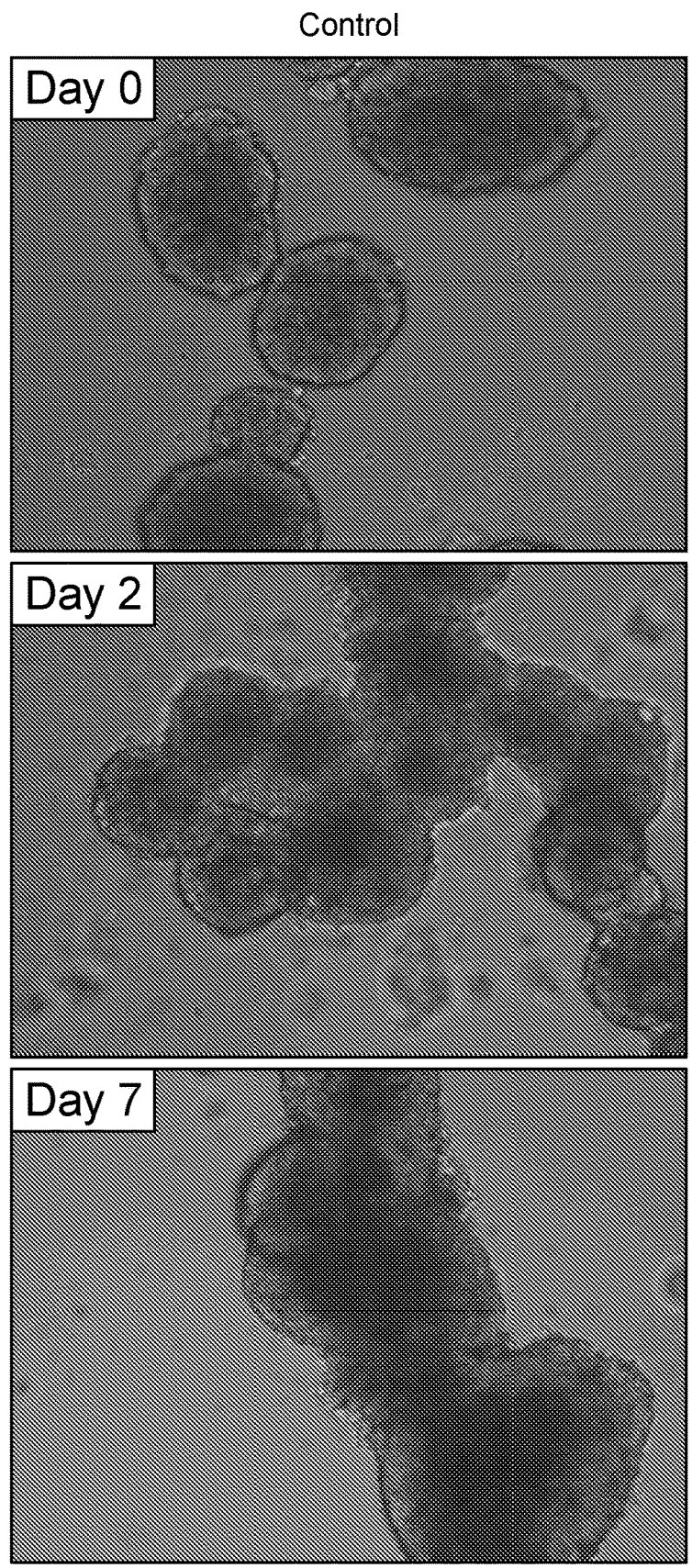
FIG. 2 shows microscopy images of cultured human islets treated with a cell culture comprising IMG (≈3 μg/mL), compared to untreated control islets. As seen with the murine islets (shown in FIG. 1), the cultured human islets treated with cell culture medium comprising active agent exhibited the same trend of migration of islet cells from the islets (Day 2) and expansion of the migrating islet cells into colonies of insulin-producing CD133 positive, Ki-67 positive proliferating islet cells (Day 7). (See Example 2)
Figure 2B:
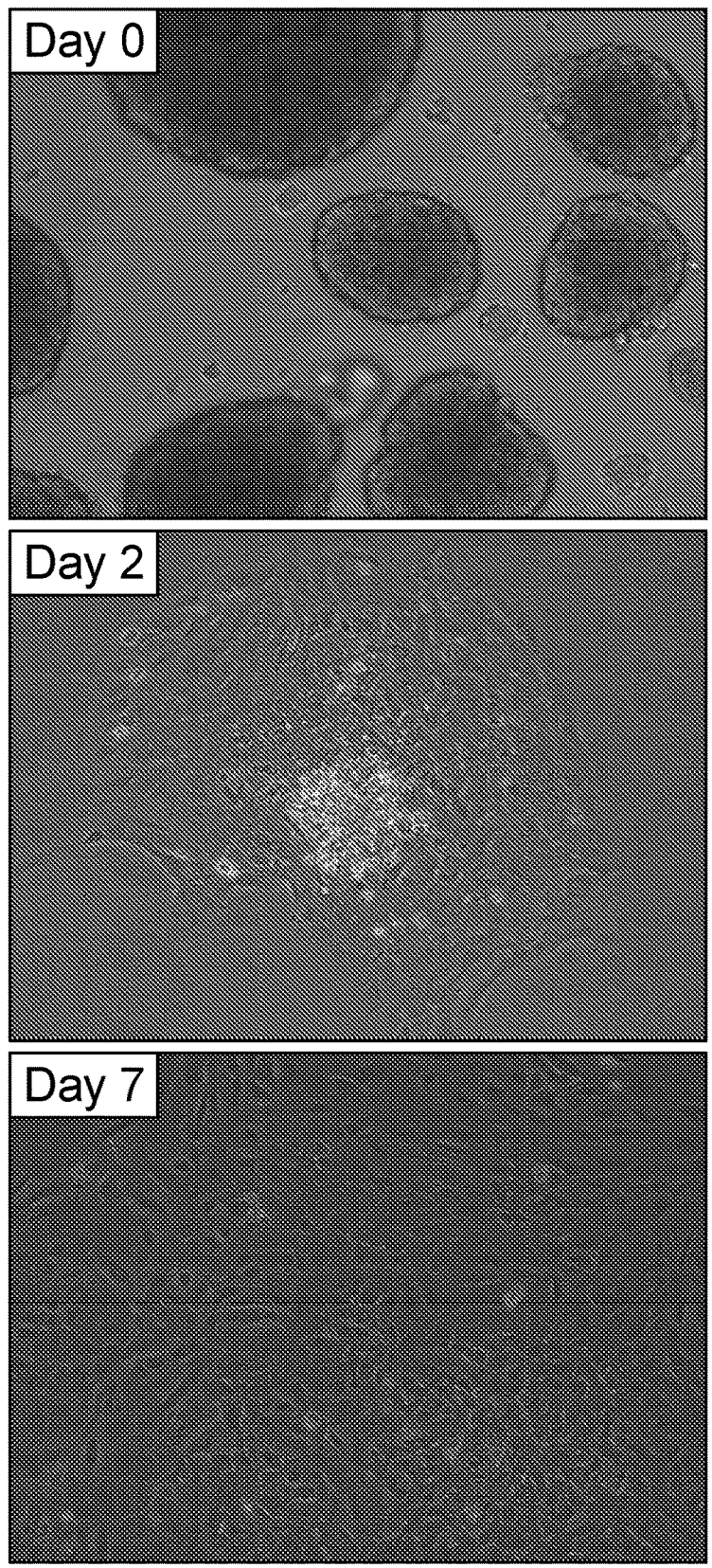
Figure 3:
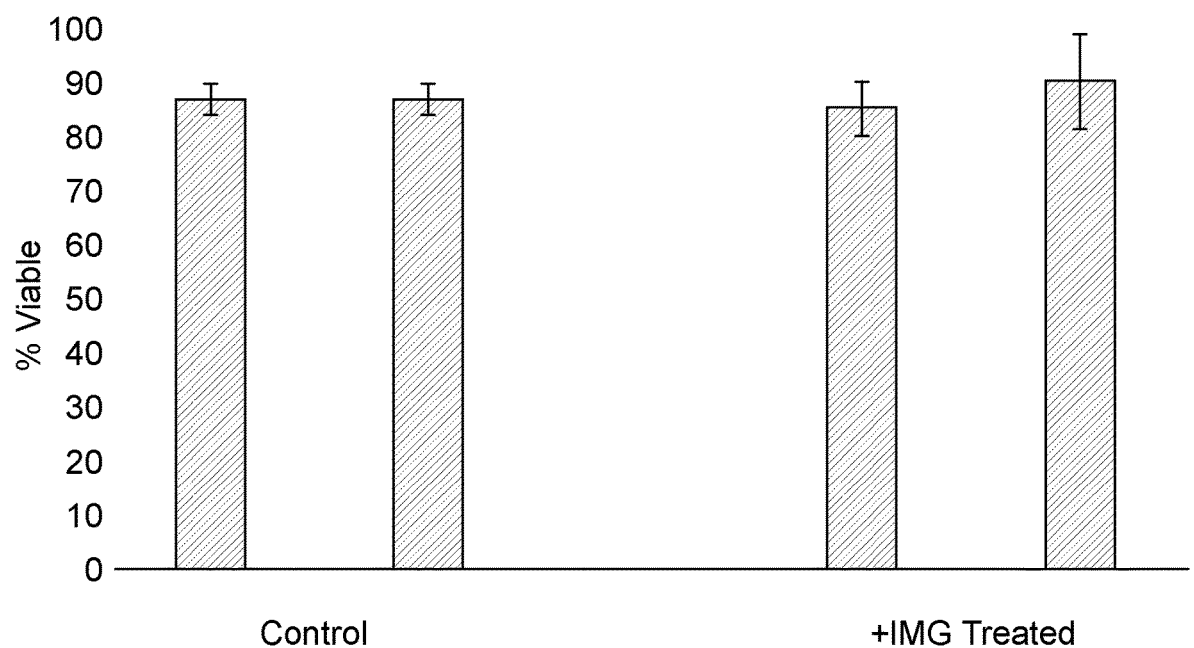
FIG. 3 shows a bar graph comparing the viability of cells as determined by propidium iodide and acridine orange staining followed by FACs, of a control cell population (untreated mouse islet cells) versus a treated cell population at days 3 and 10; both populations (control/untreated and treated cells) showed cell viability at over 80% at days 3 and 10. (See Example 1)
Figure 4A:
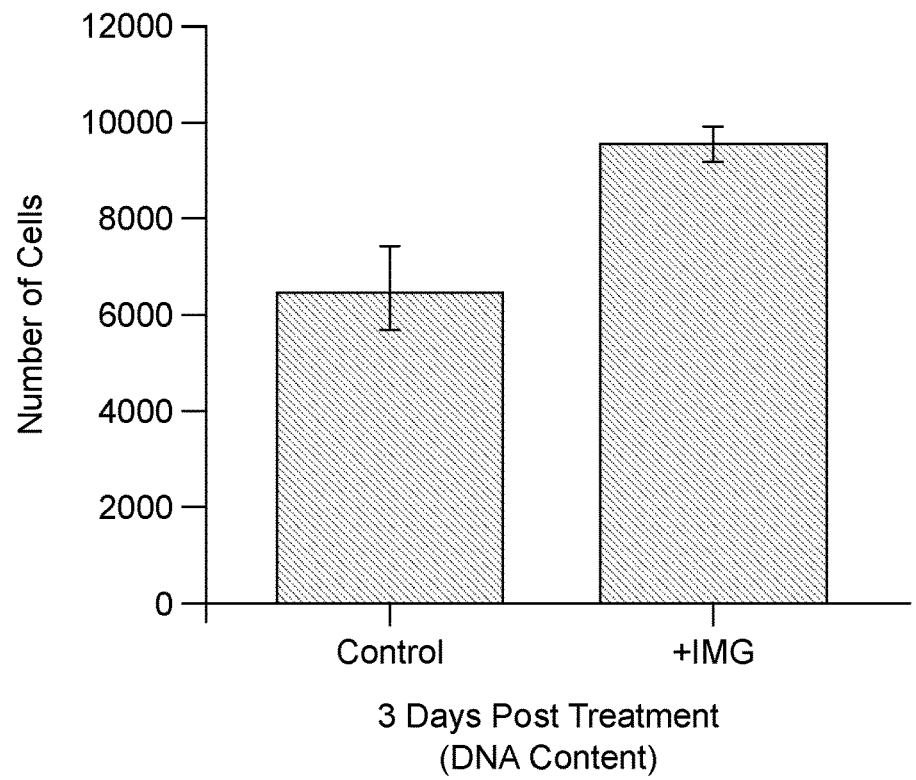
FIGS. 4A and 4B show bar graphs depicting tabulated results of the effect of culture medium comprising active agent following culture with isolated human islets; human islets cultured in medium comprising IMG (~ 10 μg/mL) resulted in an increased number of islet cells as compared to control (untreated human pancreatic islets), as determined by a CyQUANT Cell Proliferation Assays (which measures the DNA content of cells). Assays were performed 3 days post-plating of islets, and cell counting via trypan blue exclusion was done following culture of cells in medium at 10 days to determine cellular proliferation. Both means of cell measurement (cell proliferation and cell counting) showed a marked increase in the number of islet cells derived from human islets cultured in medium comprising active agent, specifically, 6,400 cells in untreated control compared to 9,500 cells following treatment with IMG (FIG. 4A); and less than 500,000 cells in untreated control compared to approximately 2,500,000 cells following treatment with IMG (FIG. 4B).
Figure 4B:
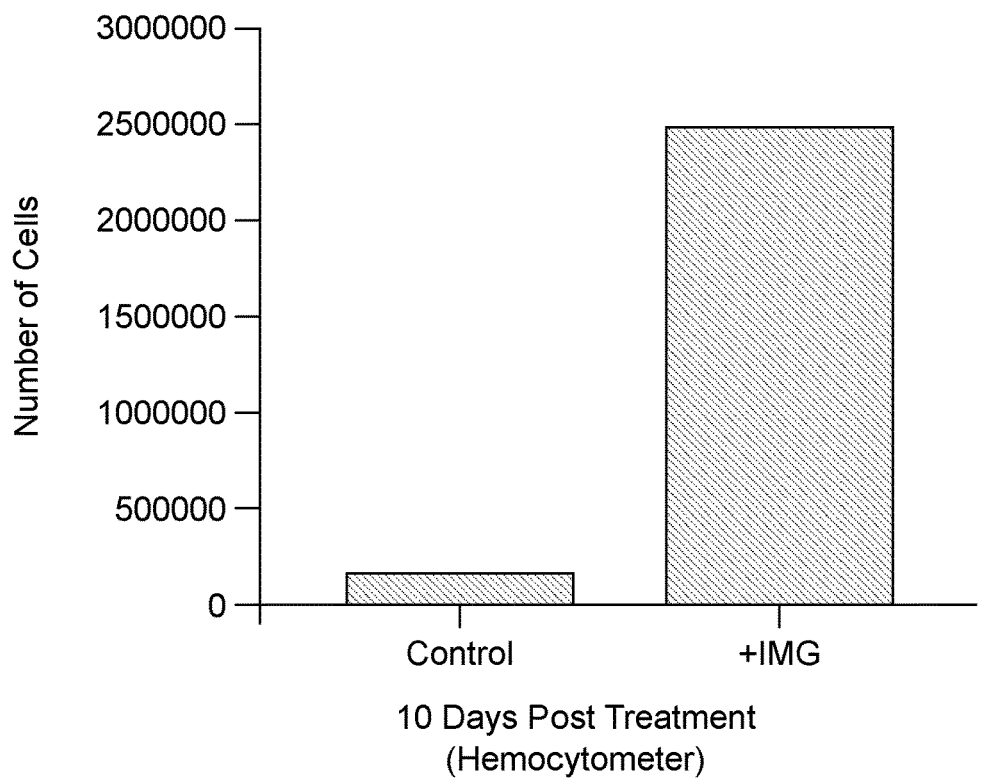
Figure 5:
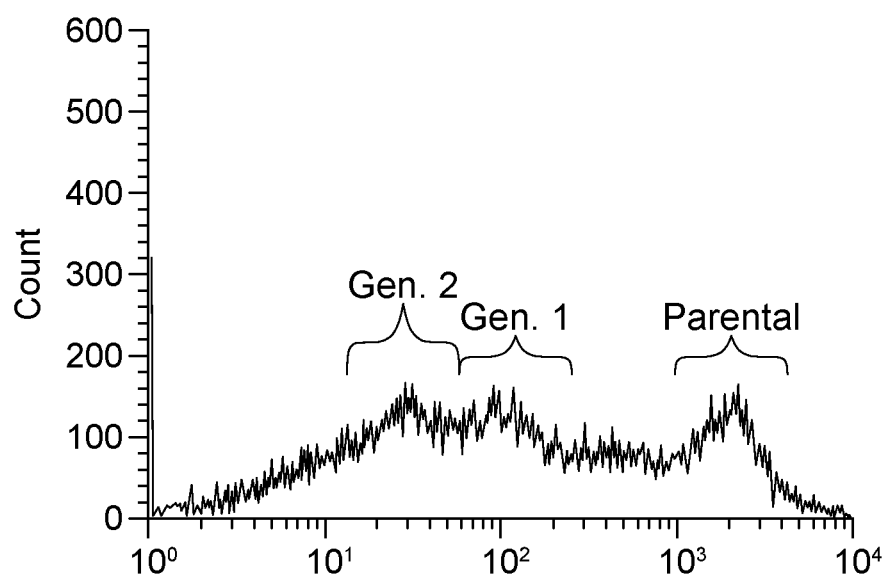
FIG. 5 shows that AIPCs generated by the treatment of isolated, non-native islets with culture medium comprising active agent (IMG) are capable of expanding beyond at least two (2) generations of progeny within five (5) days. AIPCs were labeled with Carboxyfluorescein succinimidyl ester (CFSE) and then analyzed five days post-treatment with culture medium comprising active agent using a CellTrace™ CFSE Cell Proliferation Kit. This kit is used for in vitro and in vivo labeling of cells to trace multiple generations using dye dilution by flow cytometry. Within 5 days, 2 generations of AIPCs could be observed.
Figure 6A:
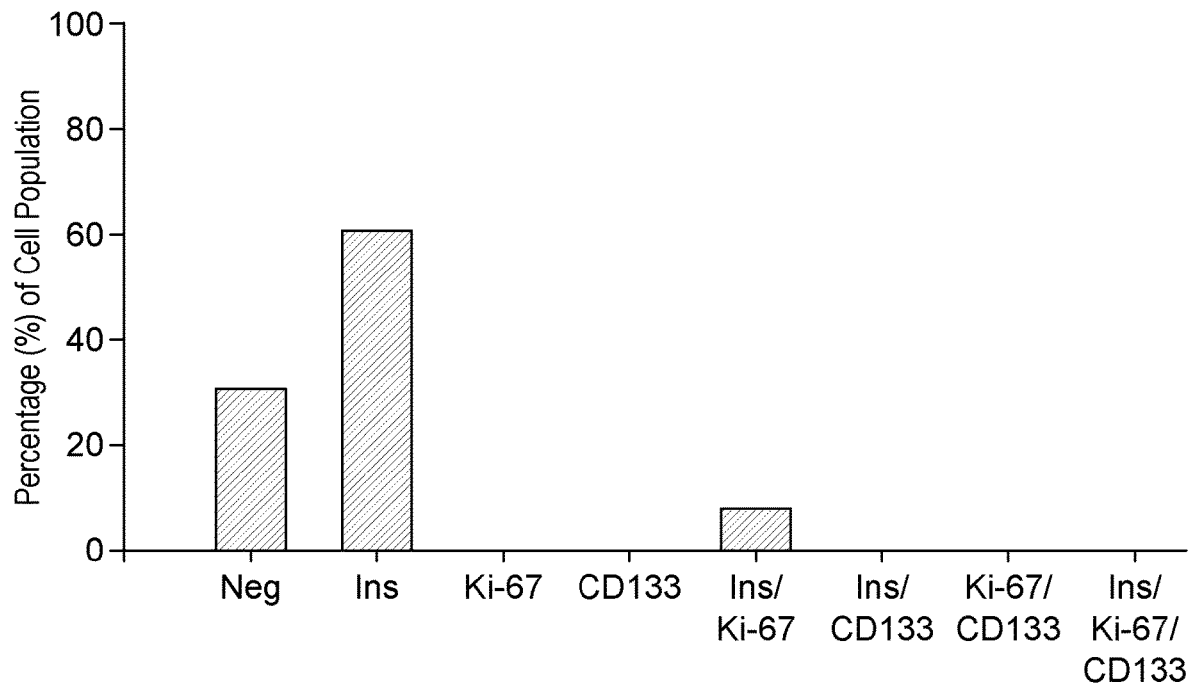
FIGS. 6A and 6B show that isolated islets cultured in medium comprising active agent (IMG) promote the expansion of islets into a population of cells (AIPCs) comprising an Insulin, CD133 and Ki-67-positive cell phenotype, as compared to control islets. Specifically, at least 60% and over 70% (the average) of isolated islets cultured in medium comprising active agent generated AIPCs that were CD133/Ki-67/insulin positive (61.47%) (see FIG. 6B); whereas the control cells exhibited less than 5% of the control cell population as CD133/Ki-67/insulin positive (essentially 0%) (see FIG. 6A). The cultured AIPCs were assessed for the expression of CD133 (a marker of somatic progenitor cells), Ki-67 (a nuclear protein associated with proliferation) and intracellular insulin expression utilizing FACs. (See Examples 1 and 2).
Figure 6B:
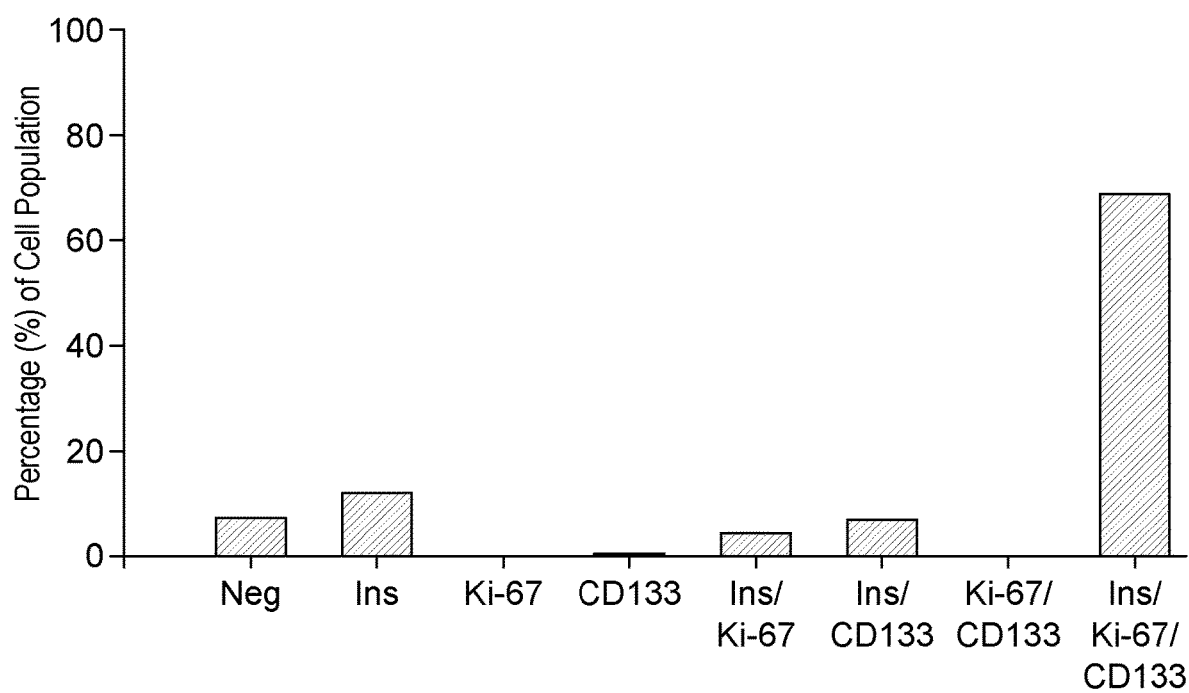

Million cells for group 1; 30 pg/Million cells for group 2; 52 pg/Million cells for group 3; 98 pg/Million cells for group 4; and 75 pg/Million cells for group 5.

Figure 9:
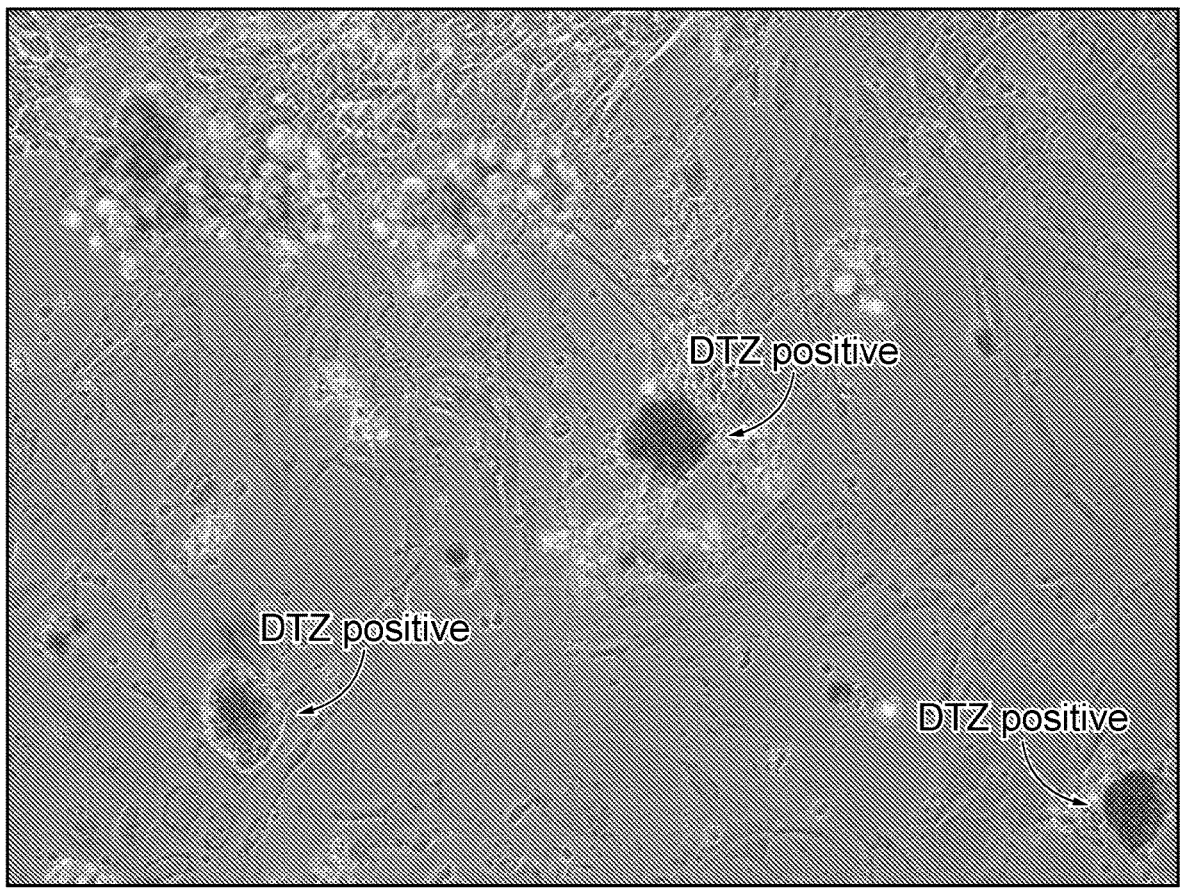

FIG. 9 shows bright field microscopy of derived AIPCs at 20 days in culture, after which time point, the derived AIPCs exhibited signs (visible in microscopy and upon staining) that the AIPCs begin generating secondary structures that resembled islets. These islet-like structures, when tested, were determined to be dithizone (DTZ) positive, representing putative beta-cells in the de-novo islets. DTZ binds zinc ions present in the islet's beta cells, and therefore stains the islets red (color results not shown).

Figure 10A:
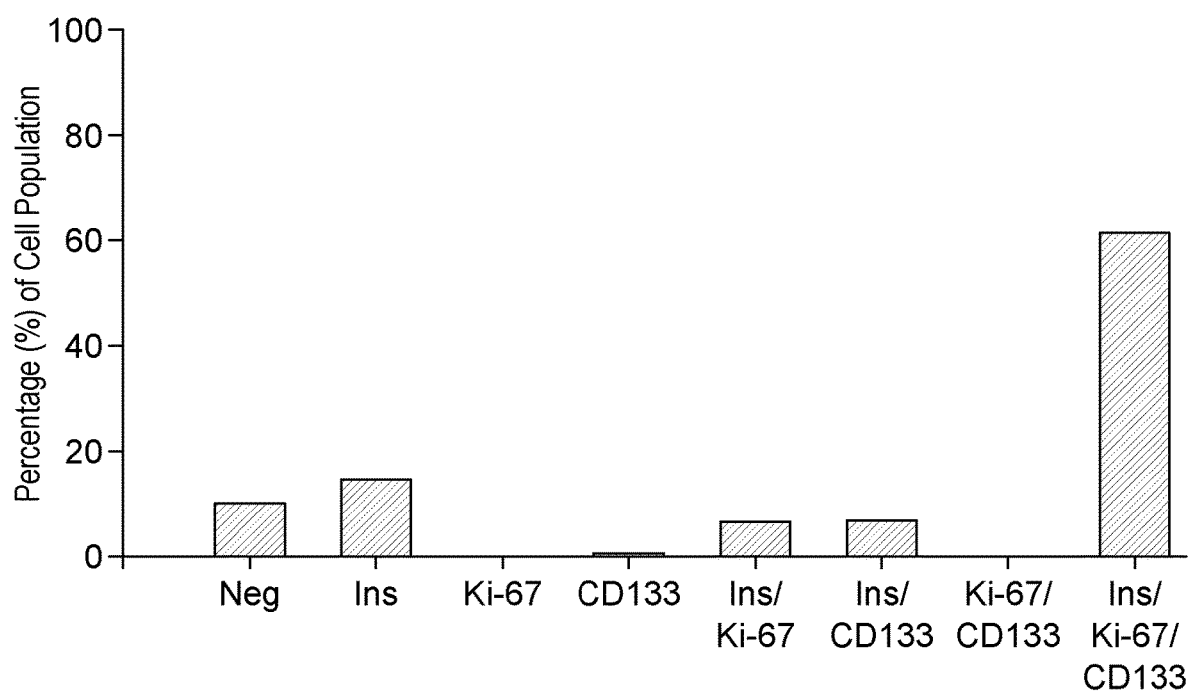
Figure 10B:
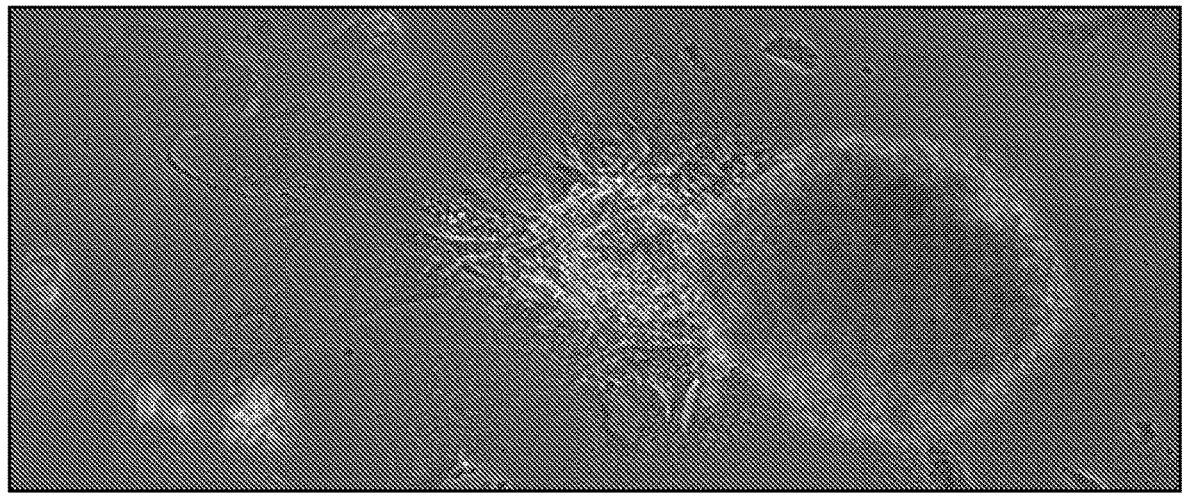
Figure 10C:
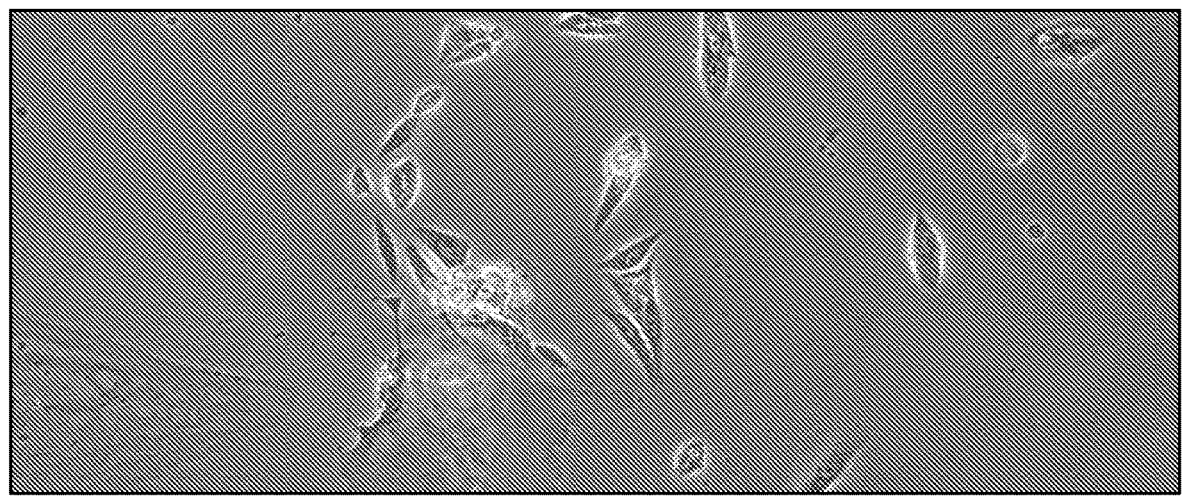

FIG. 10A shows the FACs marker profile and morphology of derived AIPCs at 60 days post-treatment with culture medium comprising active agent (IMG). The profile of AIPCs was assessed (utilizing flow cytometry as described in Example 2) after 60 days in culture and the marker as a percentage (%) of cell type was assessed. Marker profile was as follows (as a percentage of cells): Insulin-positive/Ki-67-positive/CD133-positive were shown as 61.47% of the total cell population. Approximately 10% of cells were negative for the marker profile. Furthermore, derived AIPCs expanded according to the methods herein maintained their marker profile (a CD133/Ki-67/insulin "triple" positive phenotype) and cell morphology for over 60 days in culture (FIGS. 10B and 10C).

Figure 11:
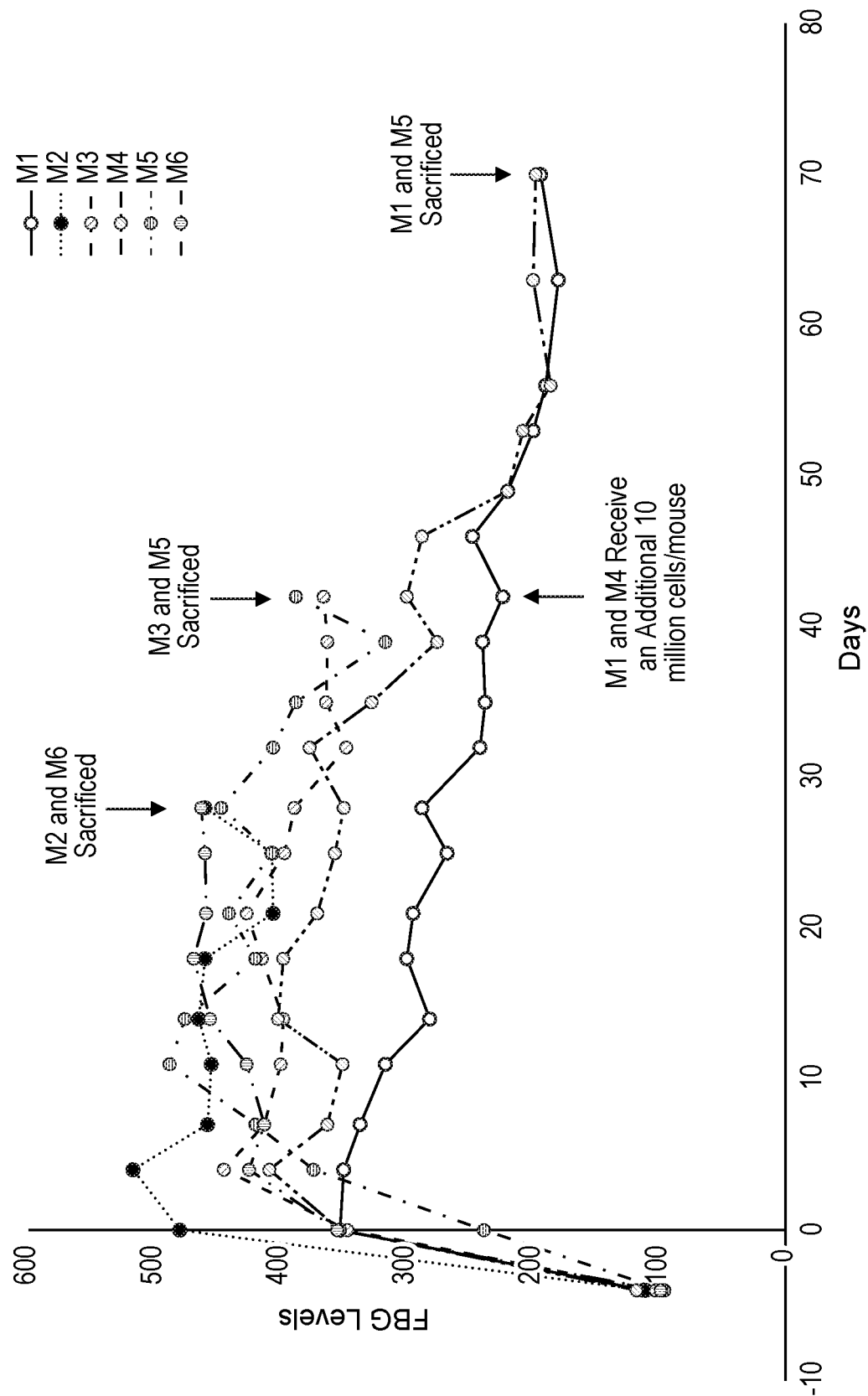

FIG. 11 shows that AIPCs remain viable in vivo and cause a reduction in blood glucose levels in a hyperglycemic mouse model (See Example 4). Four days prior to AIPCs infusion C57BL/6J mice (n=6; designated M1, M2, M3, M4, M5, M6) were treated with STZ at a concentration of 75 mg/kg. On day 0, when the animals had a fasting BG level over 200 mg/dL, each STZ-treated hyperglycemic mouse was injected with a cell suspension comprising of approximately four (4) million murine AIPCs (isolated from a Tomato Red mouse). Fasting blood glucose levels of each STZ-treated mouse were measured twice weekly; two animals were sacrificed at day 28, and two animals were sacrificed at day 42 post-administration of AIPCs. At day 46, the remaining 2 STZ-treated animals were injected with an additional (approximately) 10 million cells (each via tail vein) and sacrificed at day 70. All STZ-treated animals receiving injections of AIPCs exhibited an improvement in blood glucose levels, from 300-500 mg/dl pre-administration of AIPCs, down to approximately 200 mg/dl post-administration of AIPCs by day 50.

Figure 12:
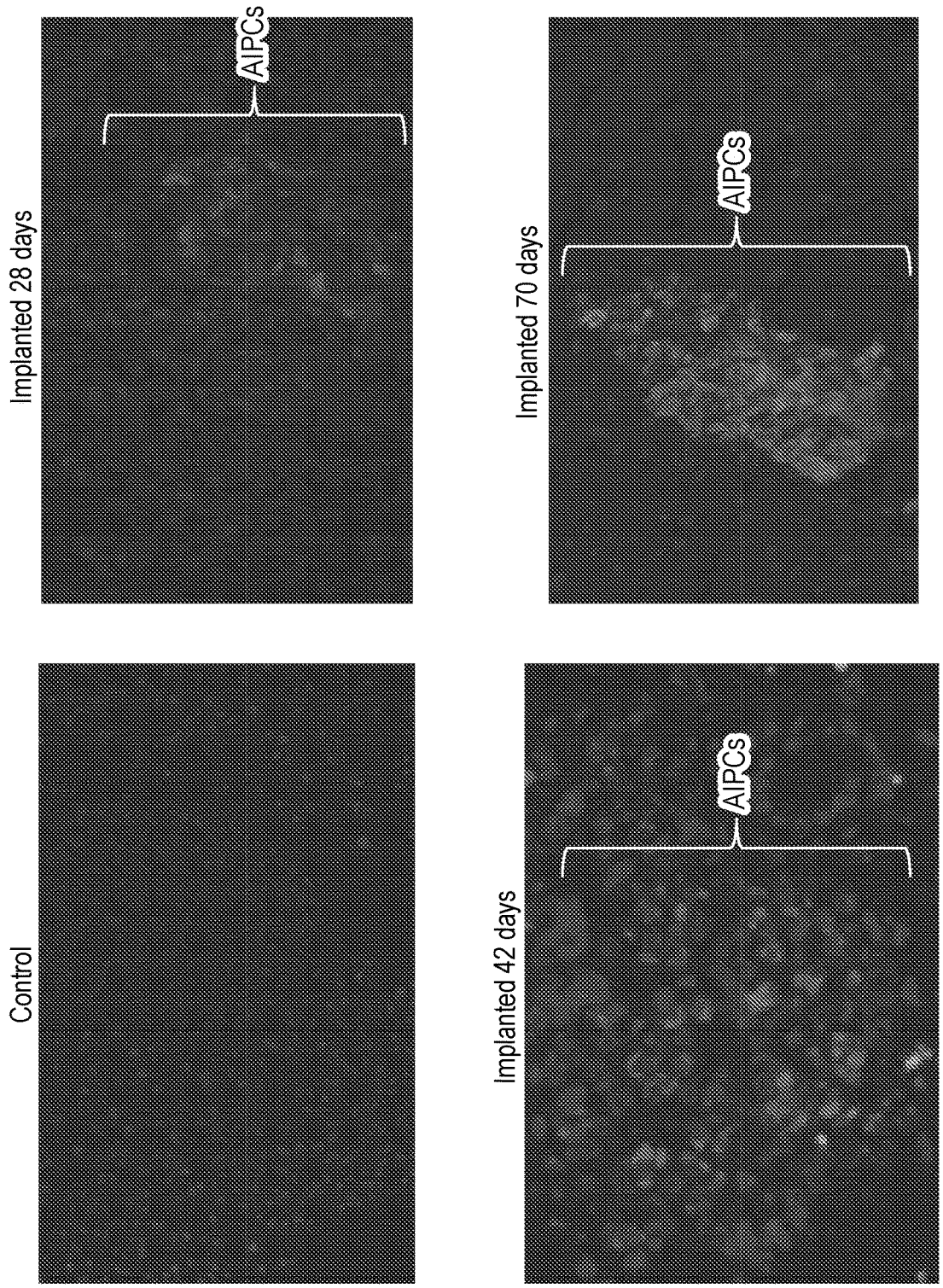

FIG. 12 shows histological analysis of sacrificed animals (Example 4) displayed donor tomato red AIPCs in the pancreas of STZ-treated animals, suggesting the migration/homing of the tail-infused AIPCs through the bloodstream to the pancreas. The AIPCs seem to be in greater concentrations at longer time periods.

Figure 13:
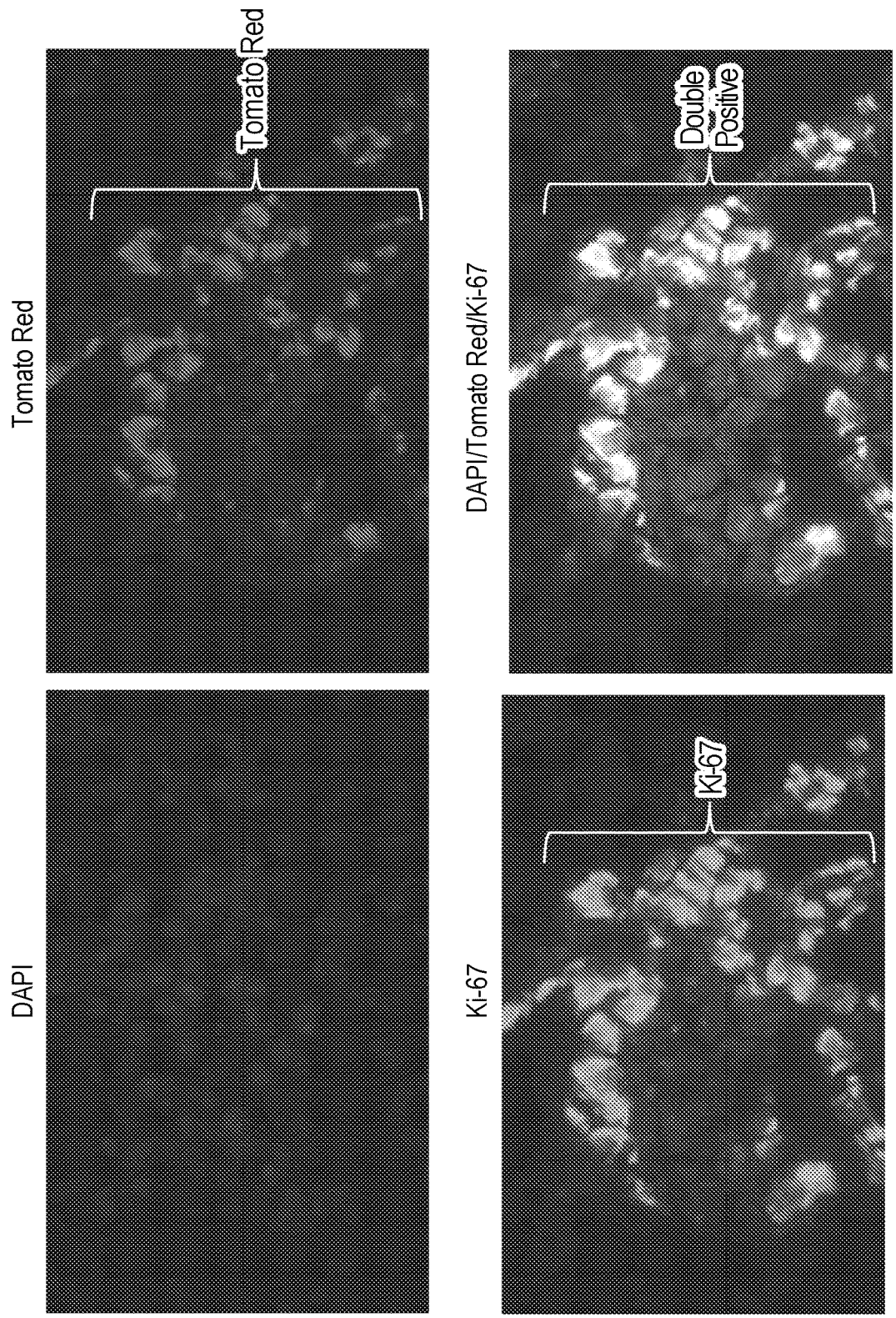

FIG. 13 shows immunohistological analysis of an AIPCs infused mouse sacrificed on day 70 (Example 4) displayed areas within the pancreas that are "double-positive" for both tomato red and Ki-67, demonstrating that the AIPCs that have homed into the pancreas can divide and propagate.

DETAILED DESCRIPTION OF THE INVENTION

Described herein are compositions and methods for promoting propagation, expansion and differentiation of a primary cell isolate comprising pancreatic islets into an endocrine progenitor cell population comprising cells positive for the markers CD133 (a marker of stem cells) and Ki-67 (a marker of active proliferation), and insulin secretion. The compositions comprise a culture medium comprising a base medium and an active agent, the active agent comprising an isolated polypeptide according to, for example, SEQ ID NO: 1, or active fragment thereof. Alternatively, the active agent may comprise an isolated polypeptide according to, for example, SEQ ID Nos: 2-4. The methods comprise the use of the culture medium to promote islet cell differentiation and the propagation of a population of endocrine progenitor cells comprising a marker profile positive for CD1331 and Ki-67 from isolated primary cells comprising pancreatic islets.

Described herein is an endocrine progenitor cell population (termed AIPC, AIPCs, or AIPC population), wherein the endocrine progenitor cell population is a) of mammalian origin; b) positive for CD133 cell marker; c) positive for Ki67 cell marker; d) insulin-producing in response to stimuli; e) generated by treating isolated primary cells comprising pancreatic islets with a culture supplement comprising an active agent comprising a polypeptide or polypeptide fragment with an amino acid sequence identity according to, for example SEQ ID NOs: 1-4.

Further methods comprise the use of the endocrine progenitor cell population produced by the methods described herein for cell transplantation or implantation, or to engineer tissue useful to treat various disorders or diseases of the pancreas.

The following terms are used in this disclosure to describe different aspects of the invention. These terms are used for explanation purposes only and are not intended to limit the scope for any aspect of the invention.

As used herein "active agent" refers to a protein, polypeptide, peptide fragment, or analogue thereof, and including any modification thereto, having an amino acid sequence having at least 50%, 55%, 60%, 65%, 70%, 75%, 80%, 85%, 90%, 95%, 98% or 99% sequence identity to the amino acid sequence according to SEQ ID NO. 01, including SEQ ID NO(s). 2-4, which represent fragments of SEQ ID NO. 1. Also, contemplated is a peptide fragment, or analogue thereof, and including any modification thereto, having an amino acid sequence having at least 50%, 55%, 60%, 65%, 70%, 75%, 80%, 85%, 90%, 95%, 98% or 99% sequence identity to the amino acid sequence according to SEQ ID NO(s): 2-4.

As used herein, the term AIPC, AIPCs, or AIPC population, refers to a non-natively derived endocrine (pancreatic) progenitor cell population generated according to the methods described herein, wherein the cell population is positive for the cell markers CD133 and Ki67 and is insulin-producing in response to stimuli.

As used herein, the term "growth" refers to the maintenance of the cells in a living state, and may include, but is not limited to, the propagation and/or differentiation of the cells. The term "propagation" refers to an increase in the number of cells present in a culture as a result of cell division.

As used herein "culture", "cultured" or "culturing" refers to removal or isolation of cells from an environment (such as in a host mammal) and their subsequent growth in a favorable artificial environment in vitro. "Cultured cells" is intended to include sub-cultured (i.e., passaged) by transferring the cells to a new vessel with fresh growth medium to provide more room for continued growth, differentiation and/or propagation.

The term "expanded" is intended to mean that the resultant cell population is derived from ex vivo culture of pancreatic islets in media compositions comprising IMG. The term "expanded" is not to be construed or limited by any mechanism or theory of cellular origin and may comprise cells that originate de novo in culture.

Reference to "pancreatic cells" include those cells normally found in the pancreas, and include pancreatic islet cells, e.g., glucagon-synthesizing alpha cells, insulin-producing beta cells, and any combination thereof. Derived AIPCs propagated from pancreatic islet cells cultured by the methods described herein are useful for, among other things, production of insulin, and implantation into a subject to treat diabetes (including, for example, type|diabetes). Pancreatic cell populations are generally not more than 3% positive for Ki-67, a cell marker used to distinguish the AIPCs generated from pancreatic cells using the methods as described herein.

The term "target site" as used herein refers to a region in the recipient host (a mammal, preferably human) that requires treatment or supplementation. The target site can be a single region within a specific organ or can be multiple regions in the host. In some embodiments, the supplementation or replacement results in the same physiological response as normal tissue, such as pancreatic tissue, whether or not targeting the pancreas.

As used herein, the terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, a "therapeutically effective amount" or "effective amount" refers to an amount that is sufficient to achieve the stated effect. A therapeutically effective amount to treat a condition is an amount of active substance capable of achieving a clinically relevant end-point in a patient or patient population. As non-limiting examples, administration of an effective amount of a composition comprising AIPCs is an amount of about 4 to about 14 million cells/kilogram, or greater than greater than 200 million cells in order to reduce a hyperglycemic subject, such as a patient suffering from hyperglycemia, to normal glycemic ranges, approximately 100 to 125 mg/dl (5.6 to 6.9 mmol/L) to under 150 mg/dL. The appropriate dose of the AIPCs formulated as a composition for injection or infusion will depend on the subject being treated and the severity of the condition to be treated. The Examples disclosed herein were, in part, conducted in murine models, and cell culture experiments utilized mammalian (human or murine) cells. Using scaling methods, such as allometric scaling, it is possible to predict suitable and exemplary dosage ranges for the administration of compositions comprising AIPCs, as disclosed herein, to adult humans. Dose scaling is an empirical approach, is well characterized and understood in the art. This approach assumes that there are some unique characteristics on anatomical, physiological, and biochemical process among species, and the possible difference in pharmacokinetics/physiological time is, as such, accounted for by scaling. As one example, not intending to be limiting, the human pancreas, based on the literature, has between six hundred thousand up to two million islets; hence there are approximately six hundred million islet cells in the normal human pancreas, with half of them being beta cells. Therefore, based on this scale a dose of four million AIPCs/kg would be expected to sufficiently replace the beta cells in a normal human pancreas.

As used herein, the term "sequence identity" refers to the identity between two or more amino acid sequences expressed in terms of the identity or similarity between the sequences. Sequence identity can be measured in terms of percentage identity; the higher the percentage, the more identical the sequences are. The percentage identity is calculated over the entire length of the sequence. Homologs or orthologs of amino acid sequences possess a relatively high degree of sequence identity when aligned using standard methods. This homology is more significant when the orthologous proteins are derived from species which are more closely related (e.g., human and mouse sequences), compared to species more distantly related (e.g., human and *C. elegans* sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Nat. Acad Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth Mol. Bio. 24:307-31, 1994. Altschul et al., J. Mol. Biol. 215:403-10, 1990, presents a detailed consideration of sequence alignment methods and homology calculations. The level of sequence identity may be determined using the NCBI Basic Local Alignment Search Tool (BLAST) (Altschul et al., J. Mol. Biol. 215:403-10, 1990), which is available from several sources, including the National Center for Biological Information (NCBI, National Library of Medicine, Building 38A, Room 8N805, Bethesda, Md. 20894, US) and on the Internet.

The active agent may be a polypeptide comprising a 293-amino acid peptide, a peptide fragment thereof, such as a peptide fragment as described in U.S. patent application Ser. No. 15/811,060, or combinations thereof; wherein the sequence of the polypeptide or fragment comprises at least 50% homology to a portion of an (293) amino acid sequence shown below and designated as SEQ ID NO: 1-4:

TABLE I

SEQ ID NO(s): 1-4:

(293 aa; fragment of approx. 31 kDa)
SEQ ID NO: 01
MADDAGAAGGPGGPGGPGMGNRGGFRGGFGSGIRGRGRGRGRGRGRG
ARGGKAEDKEWMPVTKLGRLVKDMKIKSLEEIYLFSLPIKESEIIDFFL
GASLKDEVLKIMPVQKQTRAGQRTRFKAFVAIGDYNGHVGLGVKCSKEV
ATAIRGAIILAKLSIVPVRRGYWGNKIGKPHTVPCKVTGRCGSVLVRLI
PAPRGTGIVSAPVPKKLLMMAGIDDCYTSARGCTATLGNFAKATFDAIS
KTYSYLTPDLWKETVFTKSPYQEFTDHLVKTHTRVSVQRTQAPAVATT SEQ ID NO: 2: (159 aa; fragment of approx. 17 kDa)
GHVGLGVKCSKEVATAIRGAIILAKLSIVPVRRGYWGNKIGKPHTVPCKV

TGRCGSVLVRLIPAPRGTGIVSAPVPKKLLMMAGIDDCYTSARGCTATLG

-continued

NFAKATFDAISKTYSYLTPDLWKETVFTKSPYQEFTDHLVKTHTR VSVQ

RTQAPAVATT

SEQ ID NO: 3: (75 aa; fragment of approx. 8 kDa)
SIVPVRRGYWGNKIGKPHTVPCKVTGRCGSVLVRLIPAPRGTGIVSAPV
PKKLLMMAGIDDCYTSARGCTATLGN (87 aa; fragment of approx. 9 kDa)
SEQ ID NO: 4
GHVGLGVKCSKEVATAIRGAIILAKLSIVPVRRGYWGNKIGKPHTVPCK
VTGRCGSVLVRLIPAPRGTGIVSAPVPKKLLMMAGIDD Amino acid residues of the active agents may be post-translationally modified or conjugated with other functional or non-functional molecular groups. See, e.g., Guo et al. Mol. Biosyst. 7 (7): 2286-2295, 2011, describing generally antagonistic citrullination and methylation of human ribosomal protein S2 (e.g., SEQ ID NO. 1). Naturally, such modified amino acid residues are included in the amino acid sequences and within the scope of the active agents described herein.

The polypeptides and/or polypeptide fragments according to, for example, SEQ ID NO(s): 1-4 may be produced under conditions known in the art for protein production, such as production in bacteria, yeast or by synthetic means, or as described in U.S. patent application Ser. No. 15/811,060.

A first aspect relates to a composition useful for stimulating growth, propagation and differentiation of a population of pancreatic islets into an AIPC population, wherein said composition comprises a culture medium comprising a base medium and an effective amount of an active agent, wherein the active agent comprises a polypeptide comprising an amino acid sequence according to one or more of SEQ ID NO(s): 1-4 (listed in Table 1), or active fragment thereof. In one embodiment, the polypeptide comprises an amino acid sequence having at least 50% sequence identity to the amino acid sequence set forth in SEQ ID NO: 01; in another embodiment, the polypeptide has at least 50%, 55%, 60%, 65%, 70%, 75%, 80%, 85%, 90%, 95%, 98% or 99% sequence identity to the amino acid sequence set forth in SEQ ID NO: 1. Alternatively, the polypeptide comprises an amino acid sequence having at least 50% sequence identity to the amino acid sequence set forth in any one of SEQ ID NOs: 2-4; in another embodiment, the polypeptide has at least 50%, 55%, 60%, 65%, 70%, 75%, 80%, 85%, 90%, 95%, 98% or 99% sequence identity to the amino acid sequence set forth in any one of SEQ ID NOs: 2-4.

A second aspect relates to a method for generating an AIPC population, comprising culturing a population of pancreatic islets in vitro with a cell culture medium comprising a base medium and an effective amount of an active agent. The composition may be analyzed to determine the responsiveness of the composition to glucose, such as the ability to secrete glucose when exposed to a certain amount of glucose. A feature of an AIPC population relates to the ability to secrete glucagon when exposed to appropriate stimulation.

A third aspect relates to a composition comprising an activated islet proliferating cell (AIPC) population, wherein 60% of the AIPC population is comprised of a CD133 cell marker and a Ki-67 cell marker, and wherein at least 60% of the AIPC population is capable of insulin production.

A fifth aspect relates to a composition comprising an activated islet proliferating cell (AIPC) population obtained by a method comprising culturing a population of pancreatic islets in vitro with a cell culture medium comprising a base medium and an effective amount of an active agent.

A sixth aspect relates to a method of generating an AIPC population comprising culturing a population of pancreatic islets in vitro with a cell culture medium comprising a base medium and an effective amount of an active agent to obtain the AIPC population; screening the AIPC population for one or more cell markers selective for CD133, Ki-67, and Insulin; and collecting the AIPC population identified by screening as CD133/Ki-67-positive and insulin-producing from the cultured cell population. The method of generating an AIPC population may further comprise plating the AIPC population on a suitable medium treating the cells with a culture medium comprising a base medium and an effective amount of an active agent to obtain a cultured AIPC population, passing the cultured AIPC until a a suitable percentage of the cultured AIPC population of CD133/Ki-67-positive and insulin-producing cells are propagated. Additionally, the CD133+/Ki-67+/insulin+ ("triple positive") islet cells may be packaged, formulated, or encapsulated for delivery or transplantation into a mammal (e.g., a human).

A seventh aspect relates to a method for expanding and propagating an activated islet proliferating cell ("AIPC") population, which comprises enzymatically detaching a cultured AIPC population to obtain a detached AIPC population, re-plating to a culture plate a composition comprising the detached AIPC population and a cell culture medium comprising a culture medium comprising a base medium and an active agent. A suitable protease, e.g., trypsin, may be used in said AIPCs expansion and propagation. Once detached, the AIPCs may be centrifuged at a rotational speed (e.g., 1000 rpm) and duration (e.g., 7 min) sufficient to form a pellet. It may be desirable to re-plate the detached AIPCs at a suitable cell density of, for example, about 1000 cells/cm$^2$. An interesting feature of the AIPCs, including the AIPC population, the detached AIPCs, and the like, is the viability for at least 100 days post-isolation.

An eighth aspect relates to an activated islet proliferating cell ("AIPC") population in the form of a packaged or encapsulated formulation for administration or implantation into a mammal for in vivo therapy, specifically for treatment of one or more pancreatic disorders, specifically type I diabetes. The AIPC population may be packaged as a delivery solution, or in a delivery vehicle, and administered by implantation, injection or infusion, whether administration is systemic, localized or directed to a target site.

A ninth aspect relates to a method of treating a pancreatic disorder, wherein the pancreatic disorder is hyperglycemia or diabetes type I, in a mammal, which comprises: culturing a population of pancreatic islets from a mammalian species in vitro in a culture medium comprising a base medium and an effective amount of an active agent, to obtain an AIPC population. In one embodiment, the AIPC population is comprised of insulin-producing CD133/Ki-67-positive cells. In another embodiment the method of treating a pancreatic disorder further comprises measuring the response of the AIPC population to glucose. In yet another embodiment the method of treating a pancreatic disorder further comprises expanding and propagating the AIPC population; and further comprising implanting in a mammal a composition comprising the AIPC population (e.g., predominantly insulin-producing CD133/Ki-67-positive cell population), delivering the composition to a target site, thereby providing for the treatment of the pancreatic disease. In one embodiment, the composition may be delivered as an aqueous solution, a suspension, an encapsulation, a microencapsulation, and/or an encapsulated, or semi-solid formulation; wherein the composition may be delivered to the mammal via one or more of an injection, infusion, omental or peritoneal pouch, surgical implantation, or via packaging the composition as part of a device to a target site in the mammal.

In another aspect of the invention, a composition comprises an activated islet proliferating cell (AIPC) population further comprises one or more of a buffer, one or more of a pharmaceutically acceptable carrier, or one or more of a pharmaceutically acceptable additive.

A cell culture system described herein includes at least initially, a population of pancreatic islets; a cell culture growth substrate; and a culture medium comprising a base medium and an effective amount of active agent, wherein the active agent comprises a polypeptide according to, for example, SEQ ID NO(s): 1-4, or fragment thereof, wherein the polypeptide or polypeptide fragment has a sequence identity of at least 75%, or at least 80%, or at least 85%, or at least 90%, or at least 95% with the polypeptide according to SEQ ID NO:1, e.g. 96% or more, 97% or more, 98% or more or 99% or more.

EXAMPLES

The following Examples are offered by way of illustration and not by way of limitation with respect to subject matter claimed herein. Throughout the Examples, the term "IMG" is used to reference a specific active agent, identified herein as SEQ ID NO: 1, with the understanding that the other active agents, e.g., SEQ ID NOs: 2-4, as described and defined herein may be used. Use of the term IMG and an amount thereof does not imply any specific dosage or concentration of the active agent. For the Examples, the concentrations of additives/supplements and the active agent in the culture medium are described in Table 2, while the control medium is listed in Table 3. Culture Conditions.

Cell cultures performed under the Examples were incubated at 37° C. under standard CO$_2$ (5%) conditions; culturing (plating, splitting of cells) was performed under and using standard aseptic techniques and conditions in a vertical laminar flow hood. Unless stated otherwise, AIPCs were cultured in the media described in the Tables. AIPCs were split when they reach confluency of approximately 70-80% in culture.

The splitting technique involved removal of supernatant from the culture plates (supernatant was preserved). Plates were then washed with 2-5 mL PBS (wash was preserved). AIPCs were detached using approximately 3-5 mL of Trypsin (such as available from Sigma-Aldrich) by incubating the cells in the presence of trypsin at 37° C. for approximately 3-5 minutes until cells detached. The plate is then washed a second time with PBS. The trypsinized cells, as well as the preserved PBS washes and collected cell culture supernatant, were then centrifuged at 1000 rpm for 7 minutes at 4° C. The resulting supernatant was decanted and the pellet resuspended in 2 mL PBS, and recentrifuged. The supernatant was then removed, and the pellet resuspended in Culture Medium containing IMG and re-plated at a cell density of ~1000 cells/cm$^2$.

TABLE 2

Culture Medium

| MEDIUM COMPONENT | AMOUNT |
|---|---|
| CMRL medium | 500 mL |
| L-glutamine | 2 mmol |

TABLE 2-continued

Culture Medium

| MEDIUM COMPONENT | AMOUNT |
|---|---|
| Ciprofloxacin | 2 mg/L |
| Amphotericin B | 0.1 mg/L |
| Penicillin | 100,000 units/L |
| Stretto | 100,000 micrograms/L |
| 293 amino acid polypeptides according to SEQ ID NO: 01 (IMG) | 3-20 µg/mL |
| Fetal calf serum FCS | 10% |

TABLE 3

Control Medium

| MEDIUM COMPONENT | AMOUNT |
|---|---|
| CMRL medium | 500 mL |
| Ciprofloxacin | 2 mg/L |
| Amphotericin B | 0.1 mg/L |
| Penicillin | 100,000 units/L |
| Streptomycin | 100,000 micrograms/L |
| Fetal calf serum (FCS) | 10% |

Example 1

In one exemplary study, 300 murine islets were isolated from the pancreas of male BALB/c mice (such as available from Jackson Labs or Charles River) of eight to ten weeks of age. The isolated islets were cultured in a culture medium comprising CMRL medium (originally developed by Connaught Medical Research Laboratories and now available from Mediatech, amongst others) supplemented with 10% fetal calf serum, 2 mmol L-glutamine, antibiotics and an additive comprising IMG at a concentration of about 3.0 µg/mL. The treated cells were grown alongside and compared to control cells, which were identical cells that were grown in base medium that did not contain IMG. Within 24 hours it was observed that the cells grown in the cell culture media comprising IMG became less clustered and the cultured islet cells appeared to actively migrate away from cell clusters, based upon visual inspection by microscopy at 10 times magnification (using a Leica Light Microscope with a Lumenera camera with Infinity Analyze software). On the other hand, it was observed that control islet cells maintained their clustered morphology and showed minimal evidence of cell migration. Three days post-treatment, islet cells cultured in culture medium comprising IMG showed both free-floating and attached cells in the culture. The free-floating cells were 30% viable as determined by acridine orange (AO) and propidium iodide (PI) staining. AO is an intercalating dye that can permeate both live and dead cells, while PI is a cell impermeable fluorescent solution for the exclusion of non-viable cells in flow cytometric analysis. PI binds to double stranded DNA by intercalating between base pairs but is excluded from cells with intact plasma membranes. The attached cells were 85% viable. In contrast, the control islet cell cultures exhibited no signs of free-floating cells or attached cells, although islet clusters appeared healthy, as measured by cell viability >90%. By day 10, it was shown that islet cells cultured in medium comprising IMG exhibited a low percentage of islet cell clusters, there were no discernable free-floating cells remaining in culture, and the attached cells appeared to form colonies. Total cell viability of the islet cells cultured in culture medium comprising IMG was measured at greater than 90%. While control cells continued not to exhibit migration or attachment, the islet clusters cell viability remained at around 90%. At 25 days in culture, the islet cells from both the treated and control (untreated) cultures were fixed and stained for CD133 (a marker of somatic progenitor cells) and insulin. Immunohistostaining revealed that the islet cells treated with cell culture medium comprising IMG were at least 75% insulin-positive. Furthermore, the treated islet cells were at least 70% CD133-positive; approximately 60% or more of the treated islet cells tested positive for both CD133 and insulin (deemed "double positive"). In contrast, the control cells, while 90% insulin positive, were only shown positive for the marker CD133 in less than 5% of the cell population. Likewise, less than 5% of the cell population were found to be double positive for both the CD133 marker and insulin.

The results show that the cell culture system and media described herein have the effect of inducing the activation and migration of islet cells out of the islet. These cells form colonies of CD133/insulin "double-positive" cell populations that putatively represent an activated beta-cell progenitor that may in turn be used in methods and therapeutics to regenerate damaged islets.

Example 2

In another exemplary study, human islets were utilized. Human islets, such as Human Islets for Research (HIR)®, which are primary human islets processed from organ donor pancreases are commercially available from Prodo Laboratories, Incorporated. Generally, human islet populations are less than 3% positive for Ki-67, and healthy islets are approximately 50% insulin-producing in response to stimuli. In this Example, ten (10) islets were cultured in a culture medium comprising CMRL 1066 medium, 10% fetal calf serum, 10% human serum, 2 mmol/L-glutamine, antibiotics and IMG at a concentration of about 10.0 µg/mL. Islets cultured in culture media comprising IMG were compared with control cells, which were cultured in CMRL 1066 media (alone) without IMG. The treated and untreated human islets were cultured for 5 days at 37° C. and then underwent a CyQUANT Cell Proliferation Assay (such as available from Invitrogen). Within 5 days, human islets cultured in culture medium comprising IMG were shown to have approximately 1.5 times the number of cells as the control group: 6363 cells/mL in control vs 9469 cells/mL in the islets cultured with IMG (p<0.001). Human islets cultured in media comprising IMG exhibited the same trend seen via microscopy in the Murine islets (Example 1), specifically, the islets became smaller in size, exhibited less organizational structure, and in time the islet cells appeared to actively migrate away from the clusters.

Example 3

Separately, human islets (3,000-10,000) were cultured in control media or media comprising CMRL 1066 media supplemented with 10% fetal calf serum, 10% human serum, 2 mmol/L-glutamine, antibiotics, and IMG at a concentration of 10.0 µg/mL on plates coated with an attachment factor mixture (AFM) comprising Collagen Type I (Collagen from rat tail, Sigma-Aldrich C3867) and Endothelial Cell Attachment Factor (ECAF, Sigma-Aldrich E9765). Various ratios of ECAF and collagen may be used, including a 50/50 ratio of collagen to ECAF. A thin layer of AFM (between 3-10 mL) was applied and after setting for 30 minutes the excess AFM was removed, and the plates were allowed to dry for 45 minutes in the hood. Prior to use the plates were washed with PBS to remove any potential contaminants. Cultured islets were incubated in AFM-treated flasks (plates may be used) in either culture medium or control medium for 2 to 5 days.

Control islets (cultured in standard CMRL media not containing IMG) were shown to maintain their clustered morphology and did not exhibit evidence of cell migration based on results seen using bright-field microscopy. The islet cultures (whether cultured in medium comprising IMG or cultured in standard medium) were assayed for the expression of CD133 and Ki-67 (a nuclear protein associated with proliferation), as well as intracellular insulin expression by fluorescence-activated cell sorting (FACS) using a BD FACSAria flow cytometry instrument. The cultured cells were initially labeled for CD133 expression and then the cells were fixed and permeabilized with FOXP3 Fixation/Permeabilization Buffer, as per the manufacturer's instructions, and stained with conjugated fluorometric antibodies for Ki-67 and intra-cellular insulin, respectively. FACS analysis was then following FOXP3 Fixation/Permeabilization and staining with conjugated fluorometric antibodies. Human islet cells cultured in media comprising IMG were found to be positive for CD133, Ki-67 and insulin (triple positive), specifically: greater than 80% positive for insulin, CD133 and Ki-67, while the control cells were shown to be greater than 75% positive for insulin and approximately 10-15% positive for CD133 and Ki-67.

Figure 7:
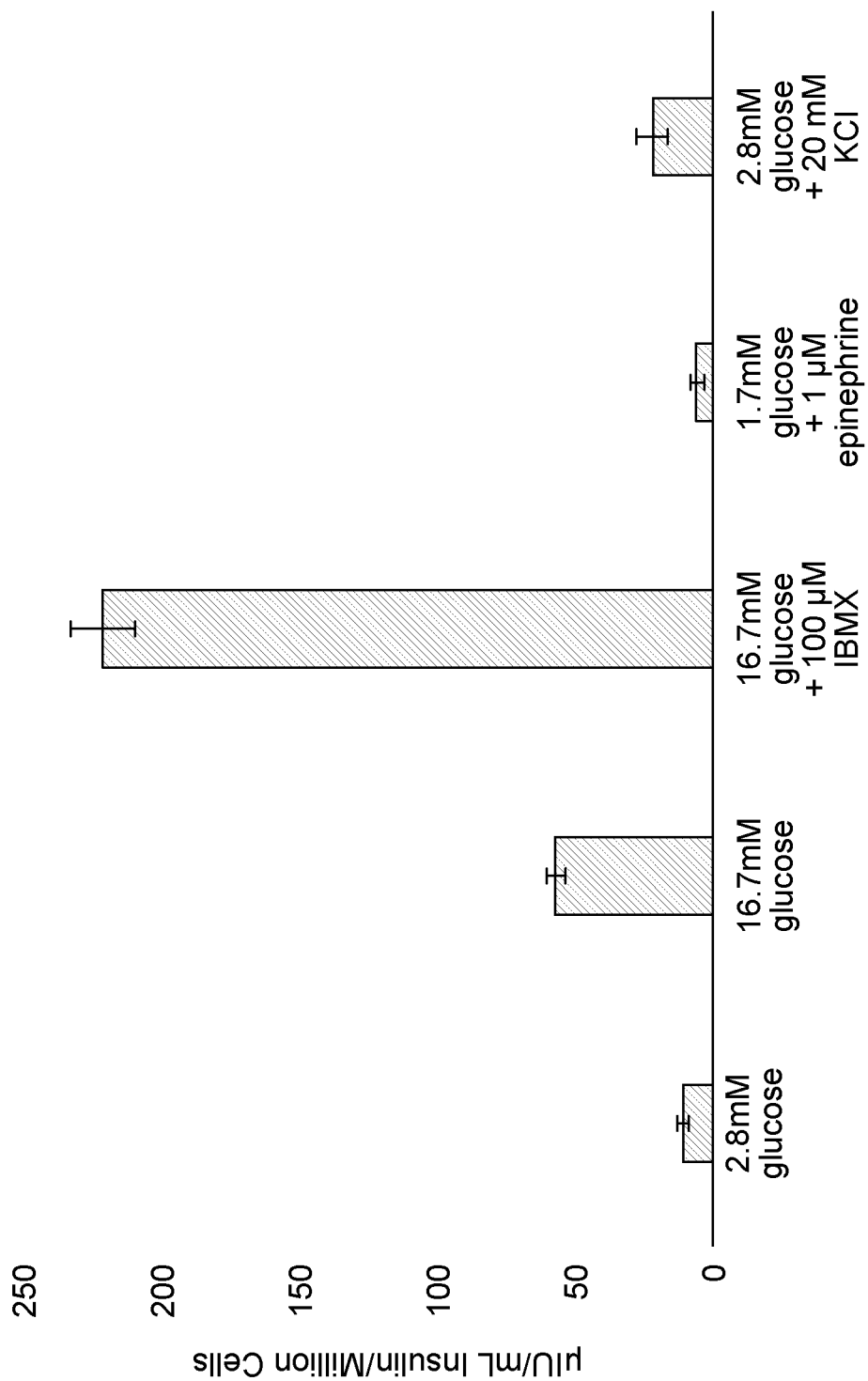
FIG. 7 shows that AIPCs derived from isolated human islets following treatment with culture medium comprising active agent secrete insulin following glucose stimulation. AIPCs were subjected to a static incubation glucose stimulated secretion assay (see Example 2). Derived AIPCs underwent 5 stimulus conditions to assess insulin secretion from the media for beta cell function. AIPCs were incubated for 30 minutes with either: (1) glucose 2.8 mM (control baseline); (2) glucose 16.7 mM (stimulus for insulin); (3) glucose 16.7 mM+100 μM IBMX (i.e., 3-isobutyl-1-methyl-xanthine, maximal stimulus for insulin); (4) glucose 1.7 mM+1 μM epinephrine (stimulus for glucagon); (5) glucose 5.6 mM+20 mM KCl (additional stimulus for insulin and glucagon). Following the assay the media was stored at −20° C. and underwent standard ELISA analysis for insulin, in which results showed insulin secretion at the level of 11 μIU/mL Insulin/Million Cells for group 1; 57 μIU/ml Insulin/Million Cells for group 2; 221 μIU/mL Insulin/Million Cells for group 3; 6 μIU/mL Insulin/Million Cells for group 4; and 22 μIU/mL Insulin/Million Cells for group 5.
Figure 8:
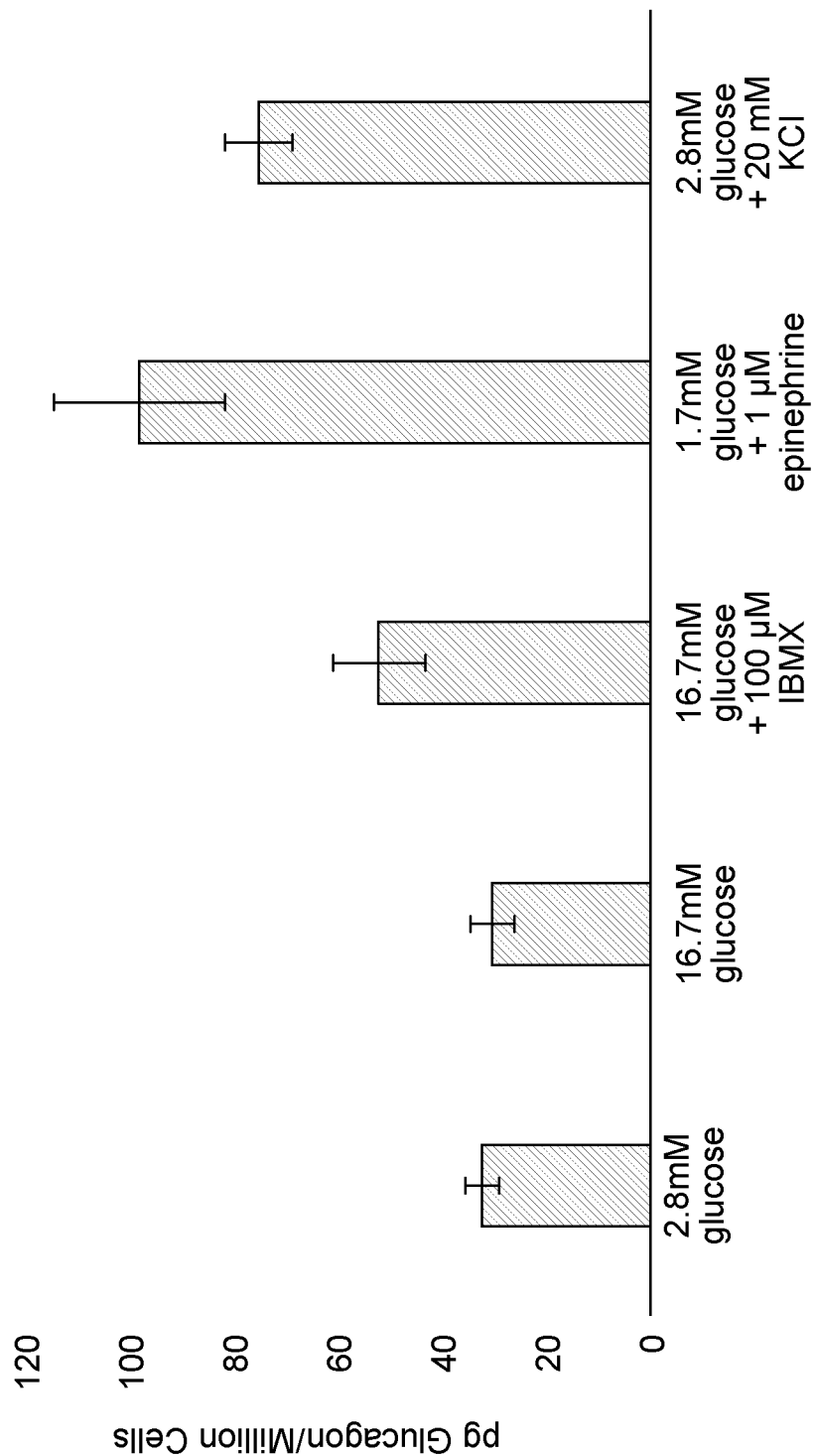
FIG. 8 shows that AIPCs derived from isolated human islets following treatment with culture medium comprising active agent secrete glucagon following glucose stimulation. AIPCs were subjected to a static incubation glucose stimulated secretion assay (see Example 2). Derived AIPCs underwent 5 stimulus conditions to assess glucagon secretion from the media for alpha cell function. AIPCs were incubated for 30 minutes with either: (1) glucose 2.8 mM (control baseline); (2) glucose 16.7 mM (stimulus for insulin); (3) glucose 16.7 mM+100 UM IBMX (maximal stimulus for insulin); (4) glucose 1.7 mM+1 μM epinephrine (stimulus for glucagon); (5) glucose 5.6 mM+20 mM KCl (additional stimulus for insulin and glucagon). Following the assay the media was stored at −20° C. and underwent standard ELISA analysis for glucagon, in which results showed glucagon secretion at the level of 32 pg glucagon/

To test glucose responsiveness of the cultured islets, AIPCs were subjected to a static incubation glucose stimulated secretion assay. Approximately $1\times10^6$ cells/well were plated in a 6-well dish and underwent 5 stimulus conditions to assess insulin secretion from the media for beta cell function, and glucagon for alpha cells function. The cells were incubated for 30 minutes with either: (1) KREB's buffer solution supplemented with physiological concentrations of glucose at 2.8 mM (control baseline); (2) glucose 16.7 mM (stimulus for insulin); (3) glucose 16.7 mM+100 µM IBMX (maximal stimulus for insulin); (4) glucose 1.7 mM+1 µM epinephrine (stimulus for glucagon); (5) glucose 5.6 mM+20 mM KCl (additional stimulus for insulin and glucagon). Following the assay the media was stored at −20° C. and underwent standard ELISA analysis for insulin and glucagon. It was shown that the islets cultured in cell culture media comprising IMG secreted insulin in response to glucose stimulation, as shown in FIGS. 7 and 8.

Example 4

To determine if AIPCs are viable in vivo and to validate AIPCs as a treatment for hyperglycemia and a method for glycemic control, six C57BL/6J mice (Jackson Labs, Stock No 000664) were treated with streptozotocin (STZ) (75 mg/kg), a chemical used for the destruction of insulin-producing cells and for the generation of type 1 Diabetes phenotypes in mice. Once the STZ-treated animals (n=6) displayed a fasting blood glucose level above 200 mg/dl, (four days post treatment with STZ) the STZ-treated mice were administered, by tail vein injection, an aqueous suspension of phosphate buffered saline (PBS) or cellular suspension comprising approximately 4 million AIPCs in 300 µL of PBS. The AIPCs used in this study were isolated from Tomato-Red mice (Jackson Labs, Stock No 007576), whose cells express robust td-Tomato fluorescence.

To generate AIPCs for the cellular suspension, murine islets were isolated from Tomato-Red mice by Type 5 collagenase digestion (as available from Sigma-Aldrich) according to methods previously published (Bertera et. al, J Transplant. 2012; 2012:856386, 2012 Dec. 9). In brief; immediately after sacrifice 2-3 mL of cold collagenase solution (1.95 mg/ml in Hank's balanced salt solution (HBSS)) was injected into the pancreas via the common bile duct. The fully inflated pancreas was removed and incubated for 20 minutes at 37° C. in a tissue culture flask, then shaken for 5 seconds to break up the tissue. The digested tissue was washed with cold HBSS supplemented with 0.2% BSA, and the islets are purified on a Ficoll gradient. Hand-picked islets were cultured in Culture Medium (Table 2) at 37° C. under standard $CO_2$ (5%) conditions. T-75 tissue culture plates were pre-treated with AFM (ECAF and Collagen Type I) prior to use as disclosed herein. Approximately 300-500 islets were plated per T-75 in Culture Medium (Table 2). Islets began to attach to the plate with cells migrating out as early as 24 hours post plating; by 72 hours most islets were attached with cells migrating out; and at approximately 7-10 days, the AIPCs were at confluency. By day 14, the AIPCs underwent serial passaging. AIPCs cultured were then collected for injection into the STZ-treated mice.

Fasting blood glucose levels of the STZ-treated mice following administration of AIPCs were measure twice weekly; 2 animals (M2 and M6) were sacrificed on day 28, and two animals (M3 and M5) were sacrificed on day 42 post-AIPCs injection. On day 46, the remaining two animals (M1 and M4) were administered, via tail vein injection, an additional 10 million cells/300 UL in suspension (PBS), and sacrificed on day 70 of the study.

Results showed that the STZ-treated AIPC-injected mice displayed a decrease in fasting blood glucose levels, that decreased over time. The final two animals (those STZ-treated mice who received two injections of AIPCs, for a total of approximately 14 million cells) exhibited normal glycemia (blood glucose levels below 200 mg/dL) by day 53 (see FIG. 11). Furthermore, histological and immunological analysis demonstrated that the AIPCs injected via tail vein into the STZ-treated mice homed to and engrafted within the pancreas, and upon engrafting into the pancreas continued to propagate, as indicated by histological staining and microscopic analysis (results shown at FIGS. 12 & 13).

Histological analysis of sacrificed animals displayed donor tomato red AIPCs in the pancreas of STZ-treated animals, suggesting the migration/homing of the tail vein infused AIPCs to the pancreas (See FIG. 12). The AIPCs seem to be in greater concentrations at longer time periods. Immunohistological analysis of STZ-treated mice receiving AIPCs via tail vein injection, and subsequently sacrificed on day 70, exhibited areas within the pancreatic tissue that were double-positive for both tomato red and Ki-67 (based on histological staining for the markers), demonstrating that the injected AIPCs homed to the pancreas where they were capable of continued cell division and propagation (See FIG. 13).

The methods described herein comprise the steps of culturing isolated islets in a cell culture medium comprising a base medium and an active agent. The culture medium showed no evidence of causing reduced viability of islet cells and showed direct evidence of promoting islet dissociation and mobilization of islet cells from the inner core of the islet. This resulting expansion of the cultured islet cells is exhibited within days when treated with the culture medium. The resulting cells expanded in the cell culture medium comprising active agent test positive for insulin expression, CD133 and Ki-67, and represent a novel AIPC cell population putatively generated using the methods and culture media described herein. The AIPCs generated by culture of isolated islets with culture medium comprising active agent were serially passaged for over 18 generations and were shown to remain viable for at least 100 days post-isolation.

A derived activated islet proliferating cell population generated according to the methods herein comprise at least 30% of CD133+/Ki-67+ cells in culture; or at least 35% of CD133+/Ki-67+ cells in culture; or at least 40% of CD133+/Ki-67+ cells in culture, or at least 45% of CD133+/Ki-67+ cells in culture; or at least 50% of CD133+/Ki-67+ cells in culture; or at least 60% of CD133+/Ki-67+ cells in culture; or at least 70% of CD133+/Ki-67+ cells in culture; or at least 80% of CD133+/Ki-67+ cells in culture, or at least 85% of CD133+/Ki-67+ cells in culture, or about 90% of CD133+/Ki-67+ cells in culture; and wherein at least 60% of the derived activated islet proliferating cells are also insulin producing.

Encapsulation of in vitro generated islet cells and implantation into a mammal have been previously characterized in the art (see, for example, Altman, et al., 1984, Trans. Am. Soc. Art. Organs 30:382-386, and U.S. Pat. No. 6,703,017 B1, herein incorporated by reference)—and would be suitable for the AIPCs generated according to the methods disclosed herein. Preferably, the encapsulant is hypoallergenic, is easily and stably situated in a target tissue, and provides added protection to the implanted cellular composition, to protect and prevent from the destruction of the implanted IPPCs.

Although the foregoing invention has been described in some detail by way of illustration and example for purposes of clarity of understanding, it will be obvious that certain changes and modifications may be practiced within the scope of the appended claims. It will be clear to a person skilled in the art that features described in relation to any of the aspects and various embodiments described above can be applicable interchangeably between the different embodiments.

The aspects of the invention and embodiments described above are examples to illustrate various features of the invention. All publications and patent applications mentioned in this application are indicative of the level of those skilled in the art to which this invention pertains. All publications and patent applications are herein incorporated by reference to the same extent as if each individual publication or patent application was specifically and individually to be incorporated by reference.

Throughout the description and claims of this specification, the words "comprise" and "contain" and variations of them mean "including but not limited to", and they are not intended to (and do not) exclude other moieties, additives, components, or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Information disclosed herein is hereby incorporated by reference, including, for example, U.S. patent application Ser. No. 15/811,060, filed on Nov. 13, 2017; PCT/GB2019/050049, filed on Jan. 9, 2019; and U.S. Provisional Patent Application No. 62/689,780 filed on Jun. 25, 2018. To the extent that terms and/or expressions incorporated herein conflict with the terms and/or expression disclosed herein, the information disclosed herein controls.

The invention claimed is:

1. A method of generating an activated islet proliferating cell (AIPC) population, comprising:
culturing a population of pancreatic islets in vitro with a cell culture medium comprising a base medium and a polypeptide according to the amino acid sequence of SEQ ID NO: 1 to obtain the AIPC population,
wherein at least 60% of the AIPC population is comprised of a CD133 cell marker and a Ki-67 cell marker;
wherein at least 60% of the AIPC population is capable of insulin production.

2. The method of claim 1, wherein the population of pancreatic islets comprise from about 10 to about 10,000 islets.

3. The method of claim 1, wherein the culturing occurs for a period of about 2 to about 10 days.

4. The method of claim 1, wherein at least about 80% of the AIPC population is positive for insulin, CD133, and Ki-67.

5. The method of claim 1, wherein the cell culture medium comprises the polypeptide at a concentration of about 1 µg/mL to about 20 µg/mL.

6. The method of claim 1, wherein the cell culture medium comprises the polypeptide at a concentration of about 5 µg/mL to about 15 µg/mL.

* * * * *